(12) United States Patent
Chen et al.

(10) Patent No.: US 9,828,423 B2
(45) Date of Patent: Nov. 28, 2017

(54) ANTI-BLYS ANTIBODY

(71) Applicants: WUHAN THERASOURCE BIOSCIENCES INC, Wuhan, Hubei (CN); SHANGHAI JUNSHI BIOSCIENCE CO., LTD, Shanghai (CN)

(72) Inventors: Bo Chen, Wuhan (CN); Hui Feng, Wuhan (CN); Hongbing Shu, Wuhan (CN)

(73) Assignees: WUHAN THERASOURCE BIOSCIENCES INC., Wuhan, Hubei Province (CN); SHANGHAI JUNSHI BIOSCIENCE CO., LTD., Shanghai (CN)

( * ) Notice: Subject to any disclaimer, the term of this patent is extended or adjusted under 35 U.S.C. 154(b) by 216 days.

(21) Appl. No.: 14/401,288

(22) PCT Filed: May 22, 2013

(86) PCT No.: PCT/CN2013/076074
§ 371 (c)(1),
(2) Date: Nov. 14, 2014

(87) PCT Pub. No.: WO2013/174264
PCT Pub. Date: Nov. 28, 2013

(65) Prior Publication Data
US 2015/0259409 A1 Sep. 17, 2015

(30) Foreign Application Priority Data
May 22, 2012 (CN) .......................... 2012 1 0160474

(51) Int. Cl.
| | | |
|---|---|---|
| *C07K 16/18* | (2006.01) | |
| *C07K 16/24* | (2006.01) | |
| *A61K 39/395* | (2006.01) | |
| *C12P 21/08* | (2006.01) | |
| *C12N 15/63* | (2006.01) | |
| *C12N 15/09* | (2006.01) | |
| *C12N 5/10* | (2006.01) | |
| *C12N 5/12* | (2006.01) | |
| *C07K 16/28* | (2006.01) | |
| *C07K 14/525* | (2006.01) | |
| *C12P 21/02* | (2006.01) | |
| *A61K 39/00* | (2006.01) | |

(52) U.S. Cl.
CPC ........ *C07K 16/241* (2013.01); *A61K 39/3955* (2013.01); *C07K 16/2875* (2013.01); *C12N 15/09* (2013.01); *C12N 15/63* (2013.01); *A61K 2039/505* (2013.01); *C07K 2317/14* (2013.01); *C07K 2317/24* (2013.01); *C07K 2317/52* (2013.01); *C07K 2317/56* (2013.01); *C07K 2317/565* (2013.01); *C07K 2317/73* (2013.01); *C07K 2317/76* (2013.01); *C12N 5/10* (2013.01); *C12N 5/12* (2013.01); *C12P 21/02* (2013.01)

(58) Field of Classification Search
CPC .......... A61K 2039/505; A61K 39/3955; A61K 39/395; A61K 2300/00; A61K 39/39558; C07K 2317/24; C07K 2317/76; C07K 2317/92; C07K 2317/565; C07K 2317/21; C07K 2317/56; C07K 2317/94; C07K 16/00; C07K 16/18; C07K 16/22; C07K 16/24
See application file for complete search history.

(56) References Cited

U.S. PATENT DOCUMENTS 8,071,092 B1 * 12/2011 Yu .......................... C07H 21/04
424/130.1
2002/0150579 A1 10/2002 Kimberly et al.
2005/0255532 A1 11/2005 Ruben et al.

FOREIGN PATENT DOCUMENTS

| CN | 1401777 A | 3/2003 |
|---|---|---|
| CN | 1279055 C | 10/2006 |
| CN | 101851291 A | 10/2010 |
| JP | 2004-509615 A | 4/2004 |
| WO | WO 98/18921 A1 * | 5/1998 |
| WO | WO-0202641 A1 | 1/2002 |
| WO | WO-03/055979 A2 | 7/2003 |
| WO | WO-2005/042009 A1 | 5/2005 |

OTHER PUBLICATIONS

"Belimumab", no author provided, Drugs R D 10(1): 55-65, 2010.*
Lied et al. Functional and clinical aspects of the B-Cell-Activating Factor (BAFF): A Narrative review. Scand J Immunol 73: 1-7, 2011.*
Mackay et al. BAFF and APRIL: A tutorial on B cell survival. Annu Rev Immunol 21: 231-264, 2003.*
Novak et al. Expression of BLyS and its receptors in B-cell non-Hodgkin lymphoma: correlation with disease activity and patient outcome. Blood 104: 2247-2253, 2004.*
Treml et al. The BLys family: toward a molecular understanding of B cell homeostasis. Cell Biochem Biophys 53:1-16, 2009.*
Stohl and Hilbert, "The discovery and development of belimumab: the anti-BLyS-lupus connection," *Nature Biotech.*, 30(1):69-77 (2012).
CN 1279055 English abstract.
(Continued)

*Primary Examiner* — Bridget E Bunner
(74) *Attorney, Agent, or Firm* — McCarter & English, LLP; Steven G. Davis; Yu Lu

(57) ABSTRACT

The present invention belongs to the field of biopharmaceutics. Disclosed is an anti-BLyS antibody. The anti-BLyS antibody specifically targets BLyS, can combine with a B lymphocyte stimulating factor, and can inhibit the combination of the B lymphocyte stimulating factor with the receptor BR3-Fc thereof. Also provided are uses of the anti-BLyS antibody in the manufacture of a medicament for preventing and/or treating diseases caused by the excessive proliferation of B cells such as systemic lupus erythematorsus.

15 Claims, 5 Drawing Sheets

(56) References Cited

OTHER PUBLICATIONS

CN 1401777 English abstract.
CN 101851291 English abstract.

* cited by examiner

SEQUENCE LISTING

```
<160> NUMBER OF SEQ ID NOS: 71

<210> SEQ ID NO 1
<211> LENGTH: 11
<212> TYPE: PRT
<213> ORGANISM: Artificial Sequence
<220> FEATURE:
<223> OTHER INFORMATION: L-CDR1 Sequence of an anti-BLyS antibody

<400> SEQUENCE: 1

Arg Ala Ser Glu Asn Ile Tyr Ser Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: L-CDR2 Sequence of an anti-BLyS antibody

<400> SEQUENCE: 2

Ala Ala Thr Asn Leu Ala Asp
1               5

<210> SEQ ID NO 3
<211> LENGTH: 9
<212> TYPE: PRT
<213> ORGANISM: Artificial Sequence
<220> FEATURE:
<223> OTHER INFORMATION: L-CDR3 Sequence of an anti-BLyS antibody

<400> SEQUENCE: 3

Gln His Phe Trp Gly Ile Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: H-CDR1 Sequence of an anti-BLyS antibody

<400> SEQUENCE: 4

Asn Thr Tyr Ile His
1               5

<210> SEQ ID NO 5
```

```
<211> LENGTH: 17
<212> TYPE: PRT
<213> ORGANISM: Artificial Sequence
<220> FEATURE:
<223> OTHER INFORMATION: H-CDR2 Sequence of an anti-BLyS antibody

<400> SEQUENCE: 5

Arg Ile Asp Leu Ala Asn Asp Tyr Ala Asn Tyr Asp Pro Lys Phe Gln
1               5                   10                  15
Asp

<210> SEQ ID NO 6
<211> LENGTH: 13
<212> TYPE: PRT
<213> ORGANISM: Artificial Sequence
<220> FEATURE:
<223> OTHER INFORMATION: H-CDR3 Sequence of an anti-BLyS antibody

<400> SEQUENCE: 6

Ser Pro Leu Thr Thr Ile Val Glu Ala Trp Phe Leu Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: L-CDR1 Sequence of an anti-BLyS antibody

<400> SEQUENCE: 7

Arg Ala Ser Ser Ser Val Ser Tyr Met His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: L-CDR2 Sequence of an anti-BLyS antibody

<400> SEQUENCE: 8

Ala Thr Ser Lys Leu Thr Ser
1               5

<210> SEQ ID NO 9
<211> LENGTH: 11
<212> TYPE: PRT
<213> ORGANISM: Artificial Sequence
<220> FEATURE:
<223> OTHER INFORMATION: L-CDR3 Sequence of an anti-BLyS antibody

<400> SEQUENCE: 9

Gln Gln Trp Ser Asn Asn Pro Arg Ile Phe Thr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: H-CDR1 Sequence of an anti-BLyS antibody

<400> SEQUENCE: 10

Ser Tyr Arg Leu His
1               5
```

```
<210> SEQ ID NO 11
<211> LENGTH: 17
<212> TYPE: PRT
<213> ORGANISM: Artificial Sequence
<220> FEATURE:
<223> OTHER INFORMATION: H-CDR2 Sequence of an anti-BLyS antibody

<400> SEQUENCE: 11

Leu Ile His Pro Asn Ser Gly Asn Thr Asn Tyr Ile Glu Lys Phe Lys
1               5                   10                  15
Ser

<210> SEQ ID NO 12
<211> LENGTH: 13
<212> TYPE: PRT
<213> ORGANISM: Artificial Sequence
<220> FEATURE:
<223> OTHER INFORMATION: H-CDR3 Sequence of an anti-BLyS antibody

<400> SEQUENCE: 12

Glu Gly Asp Leu Leu Phe Arg Lys Asp Tyr Phe Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: L-CDR1 Sequence of an anti-BLyS antibody

<400> SEQUENCE: 13

Arg Ala Ser Lys Ser Ile Ser Lys Tyr Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: L-CDR2 Sequence of an anti-BLyS antibody

<400> SEQUENCE: 14

Ser Gly Ser Ser Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: L-CDR3 Sequence of an anti-BLyS antibody

<400> SEQUENCE: 15

Gln Gln His His Glu Ser Pro Tyr Thr
1               5

<210> SEQ ID NO 16
<211> LENGTH: 5
<212> TYPE: PRT
<213> ORGANISM: Artificial Sequence
<220> FEATURE:
<223> OTHER INFORMATION: H-CDR1 Sequence of an anti-BLyS antibody

<400> SEQUENCE: 16

Asp Tyr Ala Ile His
1               5
```

<210> SEQ ID NO 17
<211> LENGTH: 17
<212> TYPE: PRT
<213> ORGANISM: Artificial Sequence
<220> FEATURE:
<223> OTHER INFORMATION: H-CDR2 Sequence of an anti-BLyS antibody

<400> SEQUENCE: 17

Trp Phe Tyr Pro Gly Ser Gly Arg Ile Lys Tyr Asn Glu Lys Phe Lys
1               5                   10                  15

Asp

<210> SEQ ID NO 18
<211> LENGTH: 19
<212> TYPE: PRT
<213> ORGANISM: Artificial Sequence
<220> FEATURE:
<223> OTHER INFORMATION: H-CDR3 Sequence of an anti-BLyS antibody

<400> SEQUENCE: 18

His Glu Trp Asp His Leu Leu Arg Ser Ser Thr Arg Gly Asp Tyr Ala
1               5                   10                  15

Leu Asp Tyr

<210> SEQ ID NO 19
<211> LENGTH: 11
<212> TYPE: PRT
<213> ORGANISM: Artificial Sequence
<220> FEATURE:
<223> OTHER INFORMATION: L-CDR1 Sequence of an anti-BLyS antibody

<400> SEQUENCE: 19

Arg Ala Ser Lys Ser Ile Ser Lys Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: L-CDR2 Sequence of an anti-BLyS antibody

<400> SEQUENCE: 20

Ser Gly Ser Thr Leu Gln Ser
1               5

<210> SEQ ID NO 21
<211> LENGTH: 9
<212> TYPE: PRT
<213> ORGANISM: Artificial Sequence
<220> FEATURE:
<223> OTHER INFORMATION: L-CDR3 Sequence of an anti-BLyS antibody

<400> SEQUENCE: 21

Gln Glu His His Glu Tyr Pro Tyr Thr
1               5

<210> SEQ ID NO 22
<211> LENGTH: 5
<212> TYPE: PRT
<213> ORGANISM: Artificial Sequence
<220> FEATURE:
<223> OTHER INFORMATION: H-CDR1 Sequence of an anti-BLyS antibody

<400> SEQUENCE: 22

Asp Tyr Thr Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: H-CDR2 Sequence of an anti-BLyS antibody

<400> SEQUENCE: 23

Trp Phe Tyr Pro Gly Asn Asp Asn Ile Lys Tyr Asn Glu Lys Phe Lys
1               5                   10                  15

Asp

<210> SEQ ID NO 24
<211> LENGTH: 19
<212> TYPE: PRT
<213> ORGANISM: Artificial Sequence
<220> FEATURE:
<223> OTHER INFORMATION: H-CDR3 Sequence of an anti-BLyS antibody

<400> SEQUENCE: 24

His Glu Trp Asp His Leu Leu Arg Ser Ser Thr Arg Gly Asp Tyr Ala
1               5                   10                  15

Met Asp Tyr

<210> SEQ ID NO 25
<211> LENGTH: 11
<212> TYPE: PRT
<213> ORGANISM: Artificial Sequence
<220> FEATURE:
<223> OTHER INFORMATION: L-CDR1 Sequence of an anti-BLyS antibody

<400> SEQUENCE: 25

Arg Thr Ser Gln Asp Ile Ser Ile Tyr Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: L-CDR2 Sequence of an anti-BLyS antibody

<400> SEQUENCE: 26

Tyr Thr Ser Arg Leu Arg Ser
1               5

<210> SEQ ID NO 27
<211> LENGTH: 9
<212> TYPE: PRT
<213> ORGANISM: Artificial Sequence
<220> FEATURE:
<223> OTHER INFORMATION: L-CDR3 Sequence of an anti-BLyS antibody

<400> SEQUENCE: 27

Gln Gln Gly Ser Thr Leu Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: H-CDR1 Sequence of an anti-BLyS antibody

```
<400> SEQUENCE: 28

Asp Ala Trp Met Asp
1               5

<210> SEQ ID NO 29
<211> LENGTH: 19
<212> TYPE: PRT
<213> ORGANISM: Artificial Sequence
<220> FEATURE:
<223> OTHER INFORMATION: H-CDR2 Sequence of an anti-BLyS antibody

<400> SEQUENCE: 29

Glu Ile Arg Asn Lys Ala Asn Asn His Ala Thr Tyr Gln Ala Glu Ser
1               5                   10                  15

Val Lys Gly

<210> SEQ ID NO 30
<211> LENGTH: 16
<212> TYPE: PRT
<213> ORGANISM: Artificial Sequence
<220> FEATURE:
<223> OTHER INFORMATION: H-CDR3 Sequence of an anti-BLyS antibody

<400> SEQUENCE: 30

Ala Pro Phe Asp Leu Leu Val Arg Arg Gly Tyr Tyr Ile Met Asp Tyr
1               5                   10                  15

<210> SEQ ID NO 31
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 31

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Lys Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Ile Pro Trp
                85                  90                  95

Thr Phe Gly Gly Gly Thr Lys Leu Glu Ile Lys
            100                 105

<210> SEQ ID NO 32
<211> LENGTH: 122
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 32

Glu Val Gln Leu Leu Gln Ser Val Ala Glu Leu Val Arg Pro Gly Ala
1               5                   10                  15
```

Ser Val Lys Leu Ser Cys Thr Thr Ser Gly Leu Asn Ile Arg Asn Thr
            20                  25                  30

Tyr Ile His Trp Val Lys Gln Arg Pro Glu Gln Gly Leu Asp Trp Ile
        35                  40                  45

Gly Arg Ile Asp Leu Ala Asn Asp Tyr Ala Asn Tyr Asp Pro Lys Phe
50                  55                  60

Gln Asp Lys Ala Thr Met Thr Val Asp Thr Ser Ser Asn Thr Ala Tyr
65                  70                  75                  80

Leu His Leu Ser Ser Leu Thr Ser Glu Asp Thr Ala Ile Tyr Tyr Cys
                85                  90                  95

Ala Gly Ser Pro Leu Thr Thr Ile Val Glu Ala Trp Phe Leu Tyr Trp
            100                 105                 110

Gly Gln Gly Thr Leu Val Thr Val Ser Ala
        115                 120

<210> SEQ ID NO 33
<211> LENGTH: 108
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 33

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Ile Pro Trp Ile Tyr
        35                  40                  45

Ala Thr Ser Lys Leu Thr Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Val Ala Thr Tyr Tyr Cys Gln Gln Trp Ser Asn Asn Pro Arg Ile
                85                  90                  95

Phe Thr Phe Gly Ser Gly Thr Lys Leu Asp Ile Arg
            100                 105

<210> SEQ ID NO 34
<211> LENGTH: 122
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 34

Gln Val Gln Leu Gln Gln Pro Gly Ala Glu Leu Val Lys Ser Gly Ala
1               5                   10                  15

Ser Val Lys Leu Ser Cys Lys Ala Ser Gly Tyr Thr Phe Thr Ser Tyr
            20                  25                  30

Arg Leu His Trp Val Lys Gln Arg Pro Gly Gln Gly Leu Asp Trp Ile
        35                  40                  45

Gly Leu Ile His Pro Asn Ser Gly Asn Thr Asn Tyr Ile Glu Lys Phe
    50                  55                  60

Lys Ser Arg Ala Thr Leu Thr Val Asp Lys Ser Ser Ser Thr Ala Tyr
65                  70                  75                  80

```
Met Gln Leu Ser Ser Leu Thr Ser Glu Asp Ser Ala Val Tyr Tyr Cys
                85                  90                  95

Ala Arg Glu Gly Asp Leu Leu Phe Arg Lys Asp Tyr Phe Asp Tyr Trp
            100                 105                 110

Gly Gln Gly Thr Thr Leu Thr Val Ser Ser
        115                 120

<210> SEQ ID NO 35
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 35

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Ser Leu Gln Ser Gly Ile Pro Ser Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Met Tyr Tyr Cys Gln Gln His His Glu Ser Pro Tyr
                85                  90                  95

Thr Phe Gly Gly Gly Thr Gln Leu Glu Ile Lys
            100                 105

<210> SEQ ID NO 36
<211> LENGTH: 128
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 36

Gln Val Gln Leu Gln Gln Ser Gly Ala Asp Leu Val Lys Pro Gly Ala
1               5                   10                  15

Ser Val Lys Leu Ser Cys Lys Ala Ser Gly Tyr Thr Phe Thr Asp Tyr
            20                  25                  30

Ala Ile His Trp Ile Lys Gln Arg Ser Gly Gln Gly Leu Glu Trp Ile
        35                  40                  45

Gly Trp Phe Tyr Pro Gly Ser Gly Arg Ile Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Trp Asp His Leu Leu Arg Ser Ser Arg Gly Asp
            100                 105                 110

Tyr Ala Leu Asp Tyr Trp Gly Gln Gly Thr Ser Val Thr Val Ser Ser
        115                 120                 125

<210> SEQ ID NO 37
```

```
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 37
```

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Ile Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Glu His His Glu Tyr Pro Tyr
                85                  90                  95

Thr Phe Gly Gly Gly Thr Thr Leu Glu Ile Lys
            100                 105

```
<210> SEQ ID NO 38
<211> LENGTH: 128
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 38
```

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Ile Lys Gln Arg Ser Gly Gln Gly Leu Asp Trp Ile
        35                  40                  45

Gly Trp Phe Tyr Pro Gly Asn Asp Asn Ile Lys Tyr Asn Glu Lys Phe
50                  55                  60

Lys Asp Lys Ala Thr Leu Thr Ala Asp Lys Ser Ser Asn Thr Val Tyr
65                  70                  75                  80

Met Glu Leu Ser Arg Leu Thr Ser Glu Asp Ser Ala Val Tyr Phe Cys
                85                  90                  95

Ala Arg His Glu Trp Asp His Leu Leu Arg Ser Ser Thr Arg Gly Asp
            100                 105                 110

Tyr Ala Met Asp Tyr Trp Gly Gln Gly Thr Ser Val Thr Val Ser Ser
        115                 120                 125

```
<210> SEQ ID NO 39
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 39
```

Asp Ile Gln Met Thr Gln Thr Thr Ser Ser Leu Ser Ala Ser Leu Gly
1               5                   10                  15

```
Asp Arg Val Thr Ile Ser Cys Arg Thr Ser Gln Asp Ile Ser Ile Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu Arg Ser Gly Val Pro Ser Arg Phe Ser Gly
 50                  55                  60

Ser Gly Ser Gly Thr Asp Phe Ser Leu Thr Ile Ser His Leu Glu Gln
65                  70                  75                  80

Glu Asp Phe Ala Thr Tyr Phe Cys Gln Gln Gly Ser Thr Leu Pro Trp
                85                  90                  95

Thr Phe Gly Gly Gly Thr Lys Leu Glu Ile Lys
            100                 105
```

<210> SEQ ID NO 40
<211> LENGTH: 126
<212> TYPE: PRT
<213> ORGANISM: Artificial Sequence
<220> FEATURE:
<223> OTHER INFORMATION: heavy chain variable region Sequence of an anti-BLyS antibody

<400> SEQUENCE: 40

```
Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Asn Lys Ala Asn Asn His Ala Thr Tyr Gln Ala Glu
 50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Pro Glu Asp Ala Gly Ile Tyr
                85                  90                  95

Tyr Cys Thr Arg Ala Pro Phe Asp Leu Leu Val Arg Arg Gly Tyr Tyr
            100                 105                 110

Ile Met Asp Tyr Trp Gly Gln Gly Thr Ser Val Thr Ser Ser
            115                 120                 125
```

<210> SEQ ID NO 41
<211> LENGTH: 106
<212> TYPE: PRT
<213> ORGANISM: Artificial Sequence
<220> FEATURE:
<223> OTHER INFORMATION: light chain variable region Sequence of an anti-BLyS antibody

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
                20                  25                  30

Leu Ala Trp Tyr Gln Gln Lys Pro Gly Lys Ala Pro Lys Leu Leu Ile
            35                  40                  45

Tyr Ala Ala Thr Asn Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln His Phe Trp Gly Ile Pro Trp
                85                  90                  95

Phe Gly Gln Gly Thr Lys Leu Glu Ile Lys
            100                 105

<210> SEQ ID NO 42
<211> LENGTH: 122
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 42

Gln Val Gln Leu Val Gln Ser Val Ala Glu Val Lys Lys Pro Gly Ala
1               5                   10                  15

Ser Val Lys Val Ser Cys Lys Ala Ser Gly Tyr Thr Phe Thr Asn Thr
            20                  25                  30

Tyr Ile His Trp Val Arg Gln Arg Pro Glu Gln Gly Leu Glu Trp Met
        35                  40                  45

Gly Arg Ile Asp Leu Ala Asn Asp Tyr Ala Asn Tyr Asp Pro Lys Phe
    50                  55                  60

Gln Asp Arg Val Thr Met Thr Arg Asp Thr Ser Thr Asn Thr Val Tyr
65                  70                  75                  80

Leu His Leu Ser Ser Leu Arg Ser Glu Asp Thr Ala Val Tyr Tyr Cys
                85                  90                  95

Ala Arg Ser Pro Leu Thr Thr Ile Val Glu Ala Trp Phe Leu Tyr Trp
            100                 105                 110

Gly Gln Gly Thr Leu Val Thr Val Ser Ser
        115                 120

<210> SEQ ID NO 43
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 43

Asp Ile Gln Met Thr Gln Ser Pro Ser Tyr Leu Ser Ala Ser Pro Gly
1               5                   10                  15

Asp Thr Val Thr Ile Asn Cys Arg Ala Ser Lys Ser Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Met Tyr Tyr Cys Gln Gln His His Glu Ser Pro Tyr
                85                  90                  95

Thr Phe Gly Gln Gly Thr Lys Leu Glu Ile Lys
            100                 105

<210> SEQ ID NO 44
<211> LENGTH: 128
<212> TYPE: PRT
<213> ORGANISM: Artificial Sequence
<220> FEATURE:

-continued

```
<223> OTHER INFORMATION: heavy chain variable region Sequence of an
      anti-BLyS antibody

<400> SEQUENCE: 44

Gln Val Gln Leu Gln Gln Ser Gly Ala Glu Leu Val Lys Pro Gly Ala
1               5                   10                  15

Ser Val Lys Val Ser Cys Lys Ala Ser Gly Tyr Thr Phe Thr Asp Tyr
            20                  25                  30

Ala Ile His Trp Val Arg Gln Arg Ser Gly Gln Gly Leu Glu Trp Met
        35                  40                  45

Gly Trp Phe Tyr Pro Gly Ser Gly Arg Ile Lys Tyr Asn Glu Lys Phe
    50                  55                  60

Lys Asp Arg Val Thr Met Thr Ala Asp Lys Ser Ser Thr Val Tyr
65                  70                  75                  80

Met Glu Leu Ser Arg Leu Thr Ser Glu Asp Thr Ala Val Tyr Tyr Cys
                85                  90                  95

Ala Arg His Glu Trp Asp His Leu Leu Arg Ser Ser Thr Arg Gly Asp
            100                 105                 110

Tyr Ala Leu Asp Tyr Trp Gly Gln Gly Thr Ser Val Thr Val Ser Ser
        115                 120                 125

<210> SEQ ID NO 45
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 45

Asp Ile Gln Met Thr Gln Ser Pro Ser Tyr Leu Ser Ala Ser Pro Gly
1               5                   10                  15

Asp Thr Val Thr Ile Asn Cys Arg Ala Ser Lys Ser Ile Ser Lys Tyr
            20                  25                  30

Leu Ala Trp Tyr Gln Gln Lys Pro Gly Lys Ala Ile Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Met Tyr Tyr Cys Gln Glu His His Glu Tyr Pro Tyr
                85                  90                  95

Thr Phe Gly Gln Gly Thr Lys Leu Glu Ile Lys
            100                 105

<210> SEQ ID NO 46
<211> LENGTH: 128
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 46

Gln Val Gln Leu Gln Gln Ser Gly Ala Glu Val Val Lys Pro Gly Ala
1               5                   10                  15

Ser Val Lys Val Ser Cys Lys Ala Ser Gly Tyr Thr Phe Thr Asp Tyr
            20                  25                  30

Thr Ile His Trp Val Arg Gln Arg Ser Gly Gln Gly Leu Glu Trp Met
```

```
                    35                  40                  45
Gly Trp Phe Tyr Pro Gly Asn Asp Asn Ile Lys Tyr Asn Glu Lys Phe
     50                  55                  60

Lys Asp Arg Val Thr Met Thr Ala Asp Lys Ser Ser Thr Val Tyr
 65                  70                  75                  80

Met Glu Leu Ser Arg Leu Thr Ser Glu Asp Thr Ala Val Tyr Tyr Cys
                 85                  90                  95

Ala Arg His Glu Trp Asp His Leu Leu Arg Ser Ser Thr Arg Gly Asp
                100                 105                 110

Tyr Ala Met Asp Tyr Trp Gly Gln Gly Thr Leu Val Thr Val Ser Ser
            115                 120                 125

<210> SEQ ID NO 47
<211> LENGTH: 107
<212> TYPE: PRT
<213> ORGANISM: Artificial Sequence
<220> FEATURE:
<223> OTHER INFORMATION: light chain variable region Sequence of an
      anti-BLyS antibody

<400> SEQUENCE: 47

Asp Ile Gln Met Thr Gln Thr Pro Ser Ser Leu Ser Ala Ser Leu Gly
  1               5                  10                  15

Asp Arg Val Thr Ile Ser Cys Arg Thr Ser Gln Asp Ile Ser Ile Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Arg Ser Gly Val Pro Ser Arg Phe Ser Gly
     50                  55                  60

Ser Gly Ser Gly Thr Asp Phe Ser Leu Thr Ile Ser Ser Leu Gln Pro
 65                  70                  75                  80

Glu Asp Phe Ala Thr Tyr Phe Cys Gln Gln Gly Ser Thr Leu Pro Trp
                 85                  90                  95

Thr Phe Gly Gly Gly Thr Lys Leu Glu Ile Lys
                100                 105

<210> SEQ ID NO 48
<211> LENGTH: 127
<212> TYPE: PRT
<213> ORGANISM: Artificial Sequence
<220> FEATURE:
<223> OTHER INFORMATION: heavy chain variable region Sequence of an
      anti-BLyS antibody

<400> SEQUENCE: 48

Glu Val Gln Leu Val Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
                 20                  25                  30

Trp Met Asp Trp Val Arg Gln Ala Pro Gly Lys Gly Leu Glu Trp Val
             35                  40                  45

Ala Glu Ile Arg Asn Lys Ala Asn Asn His Ala Thr Tyr Gln Ala Glu
     50                  55                  60

Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Ala Val Tyr
                 85                  90                  95

Tyr Cys Thr Arg Ala Pro Phe Asp Leu Leu Val Arg Arg Gly Tyr Tyr
```

```
            100                 105                 110
Ile Met Asp Tyr Trp Gly Gln Gly Thr Ser Val Thr Val Ser Ser
        115                 120                 125
```

<210> SEQ ID NO 49
<211> LENGTH: 321
<212> TYPE: DNA
<213> ORGANISM: Artificial Sequence
<220> FEATURE:
<223> OTHER INFORMATION: DNA encoding an anti-BLyS antibody fragment

<400> SEQUENCE: 49

```
gacatccaga tgactcagtc tccagcctcc ctatctgtat ctgtgggaga aactgtcacc    60
atcacatgtc gagcaagtga gaatatttac agtaatttag catggtatca gcagaaacag   120
ggaaaatctc ctcagctcct ggtctatgct gcaacaaact tagcagatgg tgtgccatca   180
aggttcagtg gcagtaaatc aggcacacag tattccctca agatcaccag cctgcagtct   240
gaagattttg ggaattatta ctgtcaacat ttttggggta ttccgtggac gttcggtgga   300
ggcaccaagc tggaaatcaa a                                             321
```

<210> SEQ ID NO 50
<211> LENGTH: 366
<212> TYPE: DNA
<213> ORGANISM: Artificial Sequence
<220> FEATURE:
<223> OTHER INFORMATION: DNA encoding an anti-BLyS antibody fragment

<400> SEQUENCE: 50

```
gaggttcaac tgctgcagtc tgtggcagag cttgtgcggc caggggcctc agtcaagttg    60
tcctgcacaa cttctggcct caacattaga aacacctata ttcactgggt gaagcagagg   120
cctgagcagg gcctggactg gattggaagg attgatcttg cgaatgatta tgctaattat   180
gacccgaagt tccaggacaa ggccactatg actgtagaca catcctccaa cacagcctac   240
ctgcacctca gcagcctgac atctgaggac actgccatct actactgtgc tggatcgccg   300
cttactacga tagtagaagc ctggtttctt tactggggcc aagggactct ggtcactgtc   360
tctgca                                                              366
```

<210> SEQ ID NO 51
<211> LENGTH: 324
<212> TYPE: DNA
<213> ORGANISM: Artificial Sequence
<220> FEATURE:
<223> OTHER INFORMATION: DNA encoding an anti-BLyS antibody fragment

<400> SEQUENCE: 51

```
caaattgttc tctcccagtc tccagcaatc ctgtctgcat ctccagggga gaaggtcaca    60
atgacttgca gggccagctc aagtgtaagt tacatgcact ggtaccagca gaagccagga   120
tcctccccca tacctggat ttatgccaca tccaagttga cttctggagt ccctgctcgc   180
ttcagtggca gtgggtctgg gacctcttac tctctcacaa tcagcagagt ggaggctgaa   240
gatgttgcca cttattactg ccagcagtgg agtaataacc cacgaatatt cacgttcggc   300
tcggggacaa agttggacat aaga                                          324
```

<210> SEQ ID NO 52
<211> LENGTH: 366
<212> TYPE: DNA
<213> ORGANISM: Artificial Sequence
<220> FEATURE:

<223> OTHER INFORMATION: DNA encoding an anti-BLyS antibody fragment

<400> SEQUENCE: 52

```
caggtccaac tgcagcagcc tggggctgag ctggtcaagt ctggggcttc agtgaagttg      60
tcctgcaagg cttctggcta cactttcacc agctaccggt tgcactgggt gaagcagagg     120
cctggccaag ccttgactg gattggacta attcatccta atagtggcaa tactaactac      180
attgagaagt tcaagagcag ggccacactg actgtagaca atcctccag cacagcctac      240
atgcaactca gcagcctgac atctgaggac tctgcggtct attactgtgc aagagagggg     300
gatttattat ccgaaaaga ctactttgac tactggggcc aaggcaccac tctcacagtc      360
tcctca                                                                 366
```

<210> SEQ ID NO 53
<211> LENGTH: 321
<212> TYPE: DNA
<213> ORGANISM: Artificial Sequence
<220> FEATURE:
<223> OTHER INFORMATION: DNA encoding an anti-BLyS antibody fragment

<400> SEQUENCE: 53

```
gatgtccaga taacccagtc tccatcttat cttgctgcat ctcctggaga aaccattact      60
attaattgca gggcaagtaa gagcattagc aaatatttag cctggtatca ggagaaacct     120
gggaaaacta taagcttct tatctactct ggatcctctt tgcaatctgg aattccatca      180
aggttcagtg gcagtggatc tggttcagat ttcactctca ccatcagtag cctggagcct     240
gaagattttg caatgtatta ctgtcaacag catcatgaat ccccgtacac gttcggggg      300
gggacccaac tggaaataaa a                                                321
```

<210> SEQ ID NO 54
<211> LENGTH: 384
<212> TYPE: DNA
<213> ORGANISM: Artificial Sequence
<220> FEATURE:
<223> OTHER INFORMATION: DNA encoding an anti-BLyS antibody fragment

<400> SEQUENCE: 54

```
caggtccaac tgcagcagtc tggagctgac ctggtgaaac ccggggcatc agtgaagctg      60
tcctgcaagg cttctggcta caccttcact gactatgcta tacattggat aaagcagagg     120
tctggacagg gtcttgagtg gattgggtgg ttttaccctg aagtggtcg tataaagtac      180
aatgagaaat tcaaagacaa ggccacattg actgcggaca atcctccag cacagtctat      240
atggagctta gtagattgac atctgaagac tctgcggtct atttctgtgc aagacacgaa     300
tgggaccatt tactacggtc gtctaccagg ggggactatg ctctggacta ttggggtcaa     360
ggaacctcag tcaccgtctc ctca                                             384
```

<210> SEQ ID NO 55
<211> LENGTH: 321
<212> TYPE: DNA
<213> ORGANISM: Artificial Sequence
<220> FEATURE:
<223> OTHER INFORMATION: DNA encoding an anti-BLyS antibody fragment

<400> SEQUENCE: 55

```
gatgtccaga taacccagtc tccatcttat cttgctgcat ctcctggaga aaccattact      60
attaattgca gggcaagtaa gagcattagc aagtatttag cctggtatca agagaaacct     120
gggaaaacta ttaagcttct tatctactct ggatccactt tacaatctgg aattccatca      180
```

```
aggttcagtg gcagtggatc tggtacagat ttcactctca ccatcagtag cctggagcct      240
gaagattttg caatgtatta ctgtcaagag catcatgaat acccgtatac gttcggaggg      300
gggaccacgc tggaaataaa a                                                321
```

<210> SEQ ID NO 56
<211> LENGTH: 384
<212> TYPE: DNA
<213> ORGANISM: Artificial Sequence
<220> FEATURE:
<223> OTHER INFORMATION: DNA encoding an anti-BLyS antibody fragment

<400> SEQUENCE: 56

```
caggtccaac tgcagcagtc tggagctgag ttggtgaaac ccggggcatc agtgaagctg       60
tcctgcaagg cttctggcta caccttcact gactatacta tacactggat aaagcagagg     120
tctggacagg gtcttgactg gattgggtgg ttttaccctg gaaatgataa tataaagtac     180
aatgagaaat tcaaggacaa ggccacattg actgcggaca atcctccaa cacagtctat      240 atggagctta gtagattgac atctgaggac tctgcggtct atttctgtgc aagacacgaa     300
tgggaccatt tactacggtc gtctaccagg ggggactatg ctatggacta ctggggtcaa     360
ggaacctcag tcaccgtctc ctca                                             384
```

<210> SEQ ID NO 57
<211> LENGTH: 322
<212> TYPE: DNA
<213> ORGANISM: Artificial Sequence
<220> FEATURE:
<223> OTHER INFORMATION: DNA encoding an anti-BLyS antibody fragment

<400> SEQUENCE: 57

```
gatatccaga tgacacagac gacatcctcc ctgtctgcct ctctgggaga cagagtcacc       60
atcagttgca ggacaagtca ggacatcagt atttatttaa actggtatca gcagaaacca     120
gatggaactg ttaaactcct gatctactac acgtcaagat tacgttcagg agtcccatca     180
aggttcagtg gcagtgggtc tggaacagat ttttctctca ccattagcca cctgaacaa      240 gaagattttg ccacttactt tgccaacag gtagtacac ttccgtggac gttcggtgga       300
ggcaccaagc tggaaatcaa ac                                               322
```

<210> SEQ ID NO 58
<211> LENGTH: 381
<212> TYPE: DNA
<213> ORGANISM: Artificial Sequence
<220> FEATURE:
<223> OTHER INFORMATION: DNA encoding an anti-BLyS antibody fragment

<400> SEQUENCE: 58

```
gaagtgaagc ttgaggaatc tggaggaggc ttggtgcaac ctggaggatc catgaaactc       60
tcttgtgctg cctctggatt cacttttagt gacgcctgga tggactgggt ccgccagtct     120
ccagagaagg ggcttgagtg ggttgctgaa attagaaaca aagctaataa tcatgcaaca     180
taccaagctg agtctgtgaa agggaggttc accatctcaa gagatgattc caaaagtagt     240
gtctacctgc aaatgaacag cttaagacct gaggacgctg catttattac ctgtaccagg     300
gccccctccg attattagt acggaggggt tactatatta tggactactg ggtcaagga      360 acctcagtca ccgtctcctc a                                                381
```

<210> SEQ ID NO 59

<211> LENGTH: 73
<212> TYPE: DNA
<213> ORGANISM: Artificial Sequence
<220> FEATURE:
<223> OTHER INFORMATION: Primer

<400> SEQUENCE: 59
tacgaagctt gcatcatcat catcatcatg gcggcggctc cggcggcggc tccccgttca    60
gggtccagaa gaa    73

<210> SEQ ID NO 60
<211> LENGTH: 46
<212> TYPE: DNA
<213> ORGANISM: Artificial Sequence
<220> FEATURE:
<223> OTHER INFORMATION: Primer

<400> SEQUENCE: 60
cgacgtcgac tcacagcagt ttcaatgcac caaaaaatgt gacatc    46

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
atggratgsa gctgkgtmat sctctt    26

<210> SEQ ID NO 62
<211> LENGTH: 39
<212> TYPE: DNA
<213> ORGANISM: Artificial Sequence
<220> FEATURE:
<223> OTHER INFORMATION: Primer

<400> SEQUENCE: 62
ggggatatcc accatgract tcgggytgag ctkggtttt    39

<210> SEQ ID NO 63
<211> LENGTH: 38
<212> TYPE: DNA
<213> ORGANISM: Artificial Sequence
<220> FEATURE:
<223> OTHER INFORMATION: Primer

<400> SEQUENCE: 63
gggtatatcc accatggctg tcttggggct gctcttct    38

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
atggagacag acacactcct gctat    25

<210> SEQ ID NO 65
<211> LENGTH: 26
<212> TYPE: DNA
<213> ORGANISM: Artificial Sequence
<220> FEATURE:
<223> OTHER INFORMATION: Primer

```
<400> SEQUENCE: 65
atggattttc aagtgcagat tttcag                                          26

<210> SEQ ID NO 66
<211> LENGTH: 27
<212> TYPE: DNA
<213> ORGANISM: Artificial Sequence
<220> FEATURE:
<223> OTHER INFORMATION: Primer

<400> SEQUENCE: 66
atggagwcac akwctcaggt ctttrta                                         27

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
atgkcccwrc tcagytyctk gt                                              22

<210> SEQ ID NO 68
<211> LENGTH: 32
<212> TYPE: DNA
<213> ORGANISM: Artificial Sequence
<220> FEATURE:
<223> OTHER INFORMATION: Primer

<400> SEQUENCE: 68
gcggaattcs aggtgmagct kcassartcw gg                                   32

<210> SEQ ID NO 69
<211> LENGTH: 60
<212> TYPE: DNA
<213> ORGANISM: Artificial Sequence
<220> FEATURE:
<223> OTHER INFORMATION: Primer

<400> SEQUENCE: 69
accgccggat ccaccaccgc ccgagccacc gccacctgcg gagacgatga ccrtggtccc     60

<210> SEQ ID NO 70
<211> LENGTH: 51
<212> TYPE: DNA
<213> ORGANISM: Artificial Sequence
<220> FEATURE:
<223> OTHER INFORMATION: Primer

<400> SEQUENCE: 70
ggtggtggat ccggcggtgg cggttccgac attgtgatga cccagtctcc a              51

<210> SEQ ID NO 71
<211> LENGTH: 33
<212> TYPE: DNA
<213> ORGANISM: Artificial Sequence
<220> FEATURE:
<223> OTHER INFORMATION: Primer

<400> SEQUENCE: 71
ggatacagtt ggtgcagcct cgagctaccg ttt                                  33
```

ANTI-BLYS ANTIBODY

CROSS-REFERENCE TO RELATED APPLICATIONS

This application is a U.S. National Stage application filed under 35 U.S.C. §371, based on International Application No. PCT/CN2013/076074, filed on May 22, 2013 and published as WO 2013/174264 A1, which claims priority to Chinese application CN 201210160474.3, filed on May 22, 2012. The contents of each of the above-referenced applications are incorporated herein by reference in their entirety.

FIELD OF THE INVENTION

The present invention belongs to the field of biopharmaceutics, and relates to an anti-BLyS antibody and the use thereof. The anti-BLyS antibody can combine with a B lymphocyte stimulating factor, and can inhibit the combination of the B lymphocyte stimulating factor with the receptor BR3-Fc thereof. It further relates to a humanized anti-BLyS antibody which has low affinity with MHC II factor and the use thereof.

BACKGROUND OF THE INVENTION

Systemic lupus erythematosus (SLE) is a kind of autoimmune disease, which involves multiple organ systems of the body such as skin, joints, heart, lung, kidney, blood and brain, and is diffusely progressive, with remission and reccurence being occurred alternatively. Systemic lupus erythematosus mainly affects African-Caribbean, Asians and Hispanics, while having minor affection on Caucasian (the white race). According to Lupus Foundation of America, it is conservatively predicted that systemic lupus erythematosus affects 300,000 people in America. Under the estimation of Datamonitor Company, there are 2.2 million patients suffered from systemic lupus erythematosus merely in China, India and Mexico, wherein patients suffered from systemic lupus erythematosus in china are more than 1 million, which is the highest in the world. Since the initial symptoms of systemic lupus erythematosus are quite larvate, the actual amount of the patients may be far more than the current estimation. Thus there are strong demands on the diagnosis and treatment of SLE in clinic.

The cause of SLE is complicated and uncertain. It is not caused by a single factor, and may be related to various factors such as heredity, environment, sex hormone and immunity, etc. At present, it is widely acknowledged by the scientific community that pathogenesis of SLE is that, at the cellular level, the self-reaction B cell stays too long in peripheral tissues, and produces human autologous antigen, which causes autoimmunity. Therefore, if it is possible to inhibit the growth and proliferation of initial B cell, the SLE can be treated.

B Lymphocyte Stimulator (BLyS), also known as Tall-1 (TNF and Apol related leukocyte expressed ligand 1), BAFF (B cell activating factor belonging to the TNF family), THANK (TNF homologues that activate apoptosis, NF-κB and JNK), belongs to tumor necrosis factor (TNF) family, and is a new cytokine firstly discovered and cloned by Hongbing Shu et al in 1999. As a co-stimulator of B Lymphocyte cell, BLyS can, in the presence of anti-IgM and IL-4, exclusively stimulate the proliferation and differentiation of B cell, and play a very important role in humoral immunity. And its over expression in the body is closely related to autoimmune disease.

Experiment in vitro shows that, after B cells are pre-activated by IgM, BLyS can induce B cells to massively proliferate and secrete large amount of IgM and IgA. However, for the B cells in rest period, this stimulation does not have obvious effect. Further study shows that, BLyS mainly acts on pre-B-lymphoid cells, immature B-lymphoid cells and activated lymphoid cells, while having no effect on plasmocyte, and lymphatic pluripotent stem cells. Like most cytokines, BLyS stimulates downstream signal transmission via the surface receptor of B cells. Many study groups confirmed that the receptors combined with BLyS are: receptor of B cell activating factor (BR3, BLyS receptor 3 or BAFF-R), transmembrane activator (transmembrane activator-1 and calcium modulator and cyclophilin ligand-interactor, TACI) and B cell maturation antigen (BCMA). This specificity determines that BLyS is a very good target for B cell antibody mediated autoimmunity diseases and lymphoma cancer.

It has been demonstrated in vivo and in vitro that the therapeutic antibody of anti-BLyS can effectively inhibit the growth of B cells, and the secretion of IgA and IgM, thereby achieving the effect of treating SLE (Edwards B M et al, The remarkable flexibility of the human antibody repertoire; isolation of over one thousand different antibodies to a single protein, BLyS. J Mol Biol. 2003 Nov. 14; 334(1):103-18; Baker K P et al, Generation and characterization of LymphoStat-B, a human monoclonal antibody that antagonizes the bioactivities of B lymphocyte stimulator. Arthritis Rheum. 2003 November; 48(11): 3253-65). Benlysta, an anti-BLyS antibody developed by US Human Genome Sciences Inc, becomes the first new medicament for SLE treatment in the past 60 years. Benlysta only aims at B cell stimulated by BLyS, and largely reduces the side effect during the therapy comparing to chemotherapy medicaments, therefore providing a safe and effective therapy for patients with SLE. Study and clinical application of targeted therapy against BLyS are developed rapidly in recent years, and most of the companies other than Human Genome Sciences Inc use fusion proteins modified on the base of BLyS or the receptor thereof. The US Genentech company developed medicament BR3-FC, Zymogenetics developed medicament TACI-FC, and AMGEN developed polypeptide-FC. In comparison with Benlysta, these medicaments have low specificity, weak binding force, relatively poor curative effect and stronger toxicity. The three medicaments are all stopped or terminated at clinical trial II. Therefore, antibody medicament of anti-BLyS is exactly the effective pharmaceutical treatment for this target.

Benlysta is produced by means of phage display library. And the disadvantages of phage display library are that: the pairing of heavy chains and light chains is thought to be artificial without in vivo selection (Greg Winter, et al., Making Antibodies by Phage Display Technology. *Annual Review of Immunology* Vol. 12: 433-455); the library is constructed from immature human PBMC, therefore the candidate antibodies have low affinity (Edwards B M, et al., The remarkable flexibility of the human antibody repertoire; isolation of over one thousand different antibodies to a single protein, BLyS. J Mol Biol. 2003 Nov. 14; 334(1):103-18); in most cases, the candidate medicaments from phage display library have drawbacks of low yield, low stability and poor pharmacokinetic character in vivo (Ponsel D, et al., High affinity, developability and functional size: the holy grail of combinatorial antibody library generation. *Molecules.* 2011 May 3; 16(5):3675-700).

Anti-BLyS antibodies with the following properties are still needed in the art: they are produced by, for example, using humanized mouse antibody technology, etc, without using phage display library; they are able to bind to B lymphocyte stimulator with high affinity and inhibit the B lymphocyte stimulator from binding to its receptor BR3-Fc, with high specificity; they have low immunogenicity; and/or they have low affinity with MHC II factor, thereby minimizing the immune response while ensuring affinity.

SUMMARY OF THE INVENTION

In one aspect, the invention provides an anti-BLyS antibody, in which the amino acid sequences of the light chains CDR1, CDR2 and CDR3 as well as the heavy chain CDR1, CDR2 and CDR3 of the anti-BLyS antibody are selected from one of the following groups or the functional variants thereof.

|   | L-CDR1 | L-CDR2 | L-CDR3 | H-CDR1 | H-CDR2 | H-CDR3 |
|---|---|---|---|---|---|---|
| A | SEQ ID NO. 1 | SEQ ID NO. 2 | SEQ ID NO. 3 | SEQ ID NO. 4 | SEQ ID NO. 5 | SEQ ID NO. 6 |
| B | SEQ ID NO. 7 | SEQ ID NO. 8 | SEQ ID NO. 9 | SEQ ID NO. 10 | SEQ ID NO. 11 | SEQ ID NO. 12 |
| C | SEQ ID NO. 13 | SEQ ID NO. 14 | SEQ ID NO. 15 | SEQ ID NO. 16 | SEQ ID NO. 17 | SEQ ID NO. 18 |
| D | SEQ ID NO. 19 | SEQ ID NO. 20 | SEQ ID NO. 21 | SEQ ID NO. 22 | SEQ ID NO. 23 | SEQ ID NO. 24 |
| E | SEQ ID NO. 25 | SEQ ID NO. 26 | SEQ ID NO. 27 | SEQ ID NO. 28 | SEQ ID NO. 29 | SEQ ID NO. 30 |

In one embodiment, the amino acid sequence of light chain variable region and the amino acid sequence of heavy chain variable region of the anti-BLyS antibody are selected from one of the following groups:

a: amino acid sequences as shown by SEQ ID NO: 31 and SEQ ID NO: 32 or the functional variants thereof;

b: amino acid sequences as shown by SEQ ID NO: 33 and SEQ ID NO: 34 or the functional variants thereof;

c: amino acid sequences as shown by SEQ ID NO: 35 and SEQ ID NO: 36 or the functional variants thereof;

d: amino acid sequences as shown by SEQ ID NO: 37 and SEQ ID NO: 38 or the functional variants thereof; and e: amino acid sequences as shown by SEQ ID NO: 39 and SEQ ID NO: 40 or the functional variants thereof.

In a preferred embodiment, the anti-BLyS antibody of the invention is humanized.

In one embodiment, the amino acid sequence of light chain variable region and the amino acid sequence of heavy chain variable region of anti-BLyS antibody are selected from one of the following groups:

I: amino acid sequences as shown by SEQ ID NO: 41 and SEQ ID NO: 42 or the functional variants thereof;

II: amino acid sequences as shown by SEQ ID NO: 43 and SEQ ID NO: 44 or the functional variants thereof;

III: amino acid sequences as shown by SEQ ID NO: 45 and SEQ ID NO: 46 or the functional variants thereof; and IV: amino acid sequences as shown by SEQ ID NO: 47 and SEQ ID NO: 48 or the functional variants thereof.

In some preferred embodiments, the anti-BLyS antibody further comprises human light chain constant region and human heavy chain constant region, and the light chain variable region and heavy chain variable region connect to human light chain constant region and human heavy chain constant region respectively. In one embodiment, the human light chain constant region is human light chain κ constant region. In one embodiment, the human heavy chain constant region is human heavy chain Fc fragment.

This invention further provides DNA molecule for coding the anti-BLyS antibody of the invention. Preferably, the DNA molecule has nucleotide sequence selected from SEQ ID NOs: 49-58.

The invention provides a recombinant DNA vector, comprising the DNA molecule of anti-BLyS antibody of the invention.

The invention further provides a host cell, comprising the recombinant DNA vector of the invention.

In another aspect, the invention provides a method for preventing and/or treating diseases caused by over proliferation of B cell, which comprises applying an effective dosage of anti-BLyS antibody of any of claims 1 to 7. In some embodiments, the diseases caused by over proliferation of B cell are selected from SLE, rheumatoid arthritis, ankylosing arthritis or B cell lymphoma cancer.

The invention further provides a pharmaceutical composition, which comprises an effective dosage of the antibody according to the invention and a pharmaceutically acceptable carrier.

The invention further provides a method of preparing anti-BLyS antibody, which comprises incubating the host cells of the invention, and obtaining the antibody.

DETAILED DESCRIPTION OF THE INVENTION

Unless otherwise defined, all the technical terms used herein have the same meaning as those understood by those skilled in the art. Regarding the definitions and terms of the art, the professionals can make reference to Current Protocols in Molecular Biology (Ausubel) specifically. The abbreviation of amino acid residue is standard code of 3 letters and/or 1 letter designating one of 20 commonly used L-amino acid in the art.

One object of the invention is to provide an anti-BLyS antibody, which can bind to B lymphocyte stimulator and inhibit its binding to receptor BR3-Fc thereof.

In order to achieve the object of the invention, the present invention adopts the following technical solutions.

By gene engineering technology, the human peripheral blood RNA is extracted, and cDNA of human BLyS is obtained by reversely transcribing with the human peripheral blood RNA being used as a template. Then gene segment of human BlyS is obtained by amplifying with the cDNA of human BLyS being used as a template respectively. And the purified protein of human BLyS is obtained by coloning the gene segment of human BlyS into eukaryotic expression system to transfect the host cells, and then expressing and purifying.

The purified protein of human BLyS is used as antigen to immunize mice so as to obtain 2000 lines of different monoclonal hybridoma cells, from which total 211 lines of clones that secrete antibodies capable of binding to BLyS protein are selected by enzyme-labeling reaction. From the 211 lines of monoclonal hybridoma cells, 5 lines of monoclonal hybridoma cells that secrete antibodies capable of inhibiting the biotin labeled BLyS from binding to receptor of BLyS on BJAB with different abilities are obtained by testing the binding capacity to receptor of BLyS on BJAB cells, which are named as 1D12, 2B10, 2G3, 5A5 and 13G8, respectively.

ELISA is used to identify the immunological characters of the antibodies secreted by the obtained 5 monoclonal hybridoma cell lines. The result shows that the antibodies secreted by monoclonal hybridoma cell lines selected by the present invention are all against BLyS specifically, without responsiveness to other antigens of TNF family such as TNF-α, TNF-β.

Further, individual monoclonal hybridoma cell RNA is extracted, and reversely transcribed to obtain cDNA, which is then, used as a template, to amplify the DNA sequence in variable region corresponding to each monoclonal hybridoma cell. After sequencing, serial analysis is conducted for the obtained sequences according to www.expasy.ch, and Kabat classification analysis is conducted based on the derived amino acid sequences, so as to determine the FR regions and CDR regions of light chain and heavy chain of antibodies secreted by each monoclonal hybridoma cell.

Since BLyS has the effect of stimulating the growth of B cell and maintaining it alive, antibodies inhibiting, especially neutralizing the effect of BLyS, will inhibit the growth of B cell. And B cell is a special type of cell for organisms to produce antibodies, so it is difficult that B cell produces antibody against the growth of itself (Thomas Schirrmann, et al., Phage display for the generation of antibodies for proteome research, diagnostics and therapy, *Molecules*, 2011, 16, 412-426). Therefore, it is relatively difficult to produce anti-BLyS antibody by means of immunizing mouse. However, the invention obtains an anti-BLyS antibody by means of immunizing mouse, and maintains the advantages of mouse antibody.

In one aspect, the invention relates to an anti-BLyS antibody, wherein the amino acid sequences of light chain CDR1, CDR2 and CDR3 as well as the heavy chain CDR1, CDR2 and CDR3 are selected from one of the following groups or the functional variants thereof.

|   | L-CDR1 | L-CDR2 | L-CDR3 | H-CDR1 | H-CDR2 | H-CDR3 |
|---|--------|--------|--------|--------|--------|--------|
| A | SEQ ID NO. 1 | SEQ ID NO. 2 | SEQ ID NO. 3 | SEQ ID NO. 4 | SEQ ID NO. 5 | SEQ ID NO. 6 |
| B | SEQ ID NO. 7 | SEQ ID NO. 8 | SEQ ID NO. 9 | SEQ ID NO. 10 | SEQ ID NO. 11 | SEQ ID NO. 12 |
| C | SEQ ID NO. 13 | SEQ ID NO. 14 | SEQ ID NO. 15 | SEQ ID NO. 16 | SEQ ID NO. 17 | SEQ ID NO. 18 |
| D | SEQ ID NO. 19 | SEQ ID NO. 20 | SEQ ID NO. 21 | SEQ ID NO. 22 | SEQ ID NO. 23 | SEQ ID NO. 24 |
| E | SEQ ID NO. 25 | SEQ ID NO. 26 | SEQ ID NO. 27 | SEQ ID NO. 28 | SEQ ID NO. 29 | SEQ ID NO. 30 |

In one embodiment, the anti-BLyS antibody secreted by said monoclonal hybridoma cell 1D12, comprises light chain variable region of amino acid sequence shown by SEQ ID NO: 31 and heavy chain variable region of amino acid sequence shown by SEQ ID NO: 32, and is named as monoclonal antibody 1D12.

In one embodiment, the anti-BLyS antibody secreted by said monoclonal hybridoma cell 2B10, comprises light chain variable region of amino acid sequence shown by SEQ ID NO: 33 and heavy chain variable region of amino acid sequence shown by SEQ ID NO: 34, and is named as monoclonal antibody 2B10.

In one embodiment, the anti-BLyS antibody secreted by said monoclonal hybridoma cell 2G3, comprises light chain variable region of amino acid sequence shown by SEQ ID NO: 35 and heavy chain variable region of amino acid sequence shown by SEQ ID NO: 36, and is named as monoclonal antibody 2G3.

In one embodiment, the anti-BLyS antibody secreted by said monoclonal hybridoma cell 5A5, comprises light chain variable region of amino acid sequence shown by SEQ ID NO: 37 and heavy chain variable region of amino acid sequence shown by SEQ ID NO: 38, and is named as monoclonal antibody 5A5.

In another embodiment, the anti-BLyS antibody secreted by said monoclonal hybridoma cell 13G8, comprises light chain variable region of amino acid sequence shown by SEQ ID NO: 39 and heavy chain variable region of amino acid sequence shown by SEQ ID NO: 40, is named as monoclonal antibody 13G8.

Certainly, without essentially affecting the activity of antibody, the skilled one in the art can replace, add and/or delete one or more (for example 1, 2, 3, 4, 5, 6, 7, 8, 9 or 10 or more) amino acids in the amino acid sequences of the invention, so as to obtain amino acid sequence with equivalent function, i.e., the functional variant of said amino acid sequence. All of these are within the scope of the invention. For example, the amino acids in the variable region can be replaced with those having similar characters.

The functional variant of amino acid sequence of the invention can share at least 95%, 96%, 97%, 98% or 99% consensus with the source sequence thereof. The sequence consensus of the invention can be measured by sequence analysis software. For example, computer programs BLAST with default parameters, especially BLASTP or TBLASTN, can be used.

For further reducing immunogenicity, the prepared mouse antibody can be humanized to obtain humanized anti-BLyS antibody. The method for preparing humanized antibody is well known to the skilled one in the art. For example, the humanized anti-BLyS antibody of the invention can be prepared by transferring the CDR sequence of the invention to variable region of human antibody. The humanized antibody will not result in anti-antibody response (AAR) and human anti mouse antibody response (HAMA), and will not be neutralized by anti-antibody and rapidly removed, thereby having immune function, such as ADCC and CDC action.

In one embodiment, the amino acid sequence of light chain variable region and amino acid sequence of heavy chain variable region of humanized anti-BLyS antibody of the invention are selected from one of the following groups:

I: amino acid sequences as shown by SEQ ID NO: 41 and SEQ ID NO: 42 or the functional variants thereof;

II: amino acid sequences as shown by SEQ ID NO: 43 and SEQ ID NO: 44 or the functional variants thereof;

III: amino acid sequences as shown by SEQ ID NO: 45 and SEQ ID NO: 46 or the functional variants thereof; and IV: amino acid sequences as shown by SEQ ID NO: 47 and SEQ ID NO: 48 or the functional variants thereof.

The humanized anti-BLyS antibody of the invention is not only able to bind to B lympocyte stimulator so as to inhibit its binding to the receptor BR3-Fc thereof, but also has low affinity to factor MHC II, thereby minimizing the immune response while maintaining affinity.

In another preferred embodiments, the anti-BLyS antibody of the invention further comprises human light chain constant region and heavy chain constant region, and the light chain variable region and heavy chain variable region connect to human light chain constant region and heavy chain constant region respectively. In one embodiment, the humanized anti-BLyS antibody comprises complete light chain and complete heavy chain, wherein the complete light chain is formed by connecting the light chain variable region contained in anti-BLyS antibody to human light chain constant region, and the complete heavy chain is formed by connecting the heavy chain variable region contained in anti-BLyS antibody to human light chain constant region.

Preferably, the human light chain constant region is the human light chain κ constant region.

Preferably, the heavy chain constant region is the human heavy chain Fc fragment.

In one embodiment, both human light chain κ constant region and human heavy chain Fc fragment are derived from healthy human B lympocyte. By gene engineering technology, the variable region and constant region are connected by overlap extension PCR to obtain complete light chain and heavy chain of humanized anti-BLyS antibody.

The invention further provides DNA molecules for coding the anti-BLyS antibody or humanized anti-BLyS antibody of the invention. Because of the degeneracy of codon, there can be many DNA molecules which can encode the antibody of the invention.

In one embodiment, the invention provides DNA molecule for coding the light chain variable region having amino acid sequences as shown by SEQ ID NO: 31, the nucleotide sequence of which is shown as SEQ ID NO: 49.

In one embodiment, the invention provides DNA molecule for coding the heavy chain variable region having amino acid sequences as shown by SEQ ID NO: 32, the nucleotide sequence of which is shown as SEQ ID NO: 50.

In one embodiment, the invention provides DNA molecule for coding the light chain variable region having amino acid sequences as shown by SEQ ID NO: 33, the nucleotide sequence of which is shown as SEQ ID NO: 51.

In one embodiment, the invention provides DNA molecule for coding the heavy chain variable region having amino acid sequences as shown by SEQ ID NO: 34, the nucleotide sequence of which is shown as SEQ ID NO: 52.

In one embodiment, the invention provides DNA molecule for coding the light chain variable region having amino acid sequences as shown by SEQ ID NO: 35, the nucleotide sequence of which is shown as SEQ ID NO: 53.

In one embodiment, the invention provides DNA molecule for coding the heavy chain variable region having amino acid sequences as shown by SEQ ID NO: 36, the nucleotide sequence of which is shown as SEQ ID NO: 54.

In one embodiment, the invention provides DNA molecule for coding the light chain variable region having amino acid sequences as shown by SEQ ID NO: 37, the nucleotide sequence of which is shown as SEQ ID NO: 55.

In one embodiment, the invention provides DNA molecule for coding the heavy chain variable region having amino acid sequences as shown by SEQ ID NO: 38, the nucleotide sequence of which is shown as SEQ ID NO: 56.

In one embodiment, the invention provides DNA molecule for coding the light chain variable region having amino acid sequences as shown by SEQ ID NO: 39, the nucleotide sequence of which is shown as SEQ ID NO: 57.

In one embodiment, the invention provides DNA molecule for coding the heavy chain variable region having amino acid sequences as shown by SEQ ID NO: 40, the nucleotide sequence of which is shown as SEQ ID NO: 58.

The term "anti-BLyS antibody" used herein comprises any antibody or immunoglobulin of phenogen, or antigen-binding fragment which retains the specific binding capacity to antigen, including but not limited to Fv, scFv (sc means single chain), Fab, F(ab')2, Fab', scFv-Fc fragment, diabody, chimeric antibody, single chain antibody, and fusion protein comprising antigen-binding part of the antibody and non-antibody protein. The antibody can be labeled and detected, for example, by radioactive isotope, enzyme which can produce detectable substance, fluorescent protein, biotin, etc. The antibody can also bind to solid phase carrier, including but not limited to polystyrene plate or bead, etc.

Further, the DNA molecule for coding the anti-BLyS antibody of the invention can be cloned into the vector by the skilled one in the art, so as to transform host cells. Therefore, the invention further provides a recombinant DNA vector, which comprises DNA molecule for coding the anti-BLyS antibody of the invention.

Preferably, the recombinant DNA vector is an expression vector, into which the DNA molecule of said antibody is cloned by the skilled one in the art, so as to transform host cell and obtain single chain antibody by inducing expression.

In one embodiment, the recombinant DNA vector of the invention comprises DNA molecule for coding the humanized anti-BLyS antibody of the invention. The DNA molecule of the coded humanized anti-BLyS antibody can be recombined to construct vector for mammal transcription and expression. The expression vector of the invention comprises the DNA sequence of the variable region and constant region of the heavy chain and light chain of the coded human anti-BlyS monoclonal antibody. However, two expression vectors can be constructed respectively, one comprising heavy chain variable region and constant region, the other comprising light chain variable chain and constant chain, to transfect the mammals together.

In a preferred embodiment, the expression vector further comprises a promoter and a DNA sequence for coding secreting signal peptides, and at least one medicament resistant gene for screening. The method used comprises DNA synthesis technology and in vitro recombinant technology.

The invention further provides a host cell, comprising the recombinant DNA vector of the invention. The host cell of the invention can be prokaryotic host cell, eukaryotic host cell or bacteriophage.

In particular, the prokaryotic host cell can be *Escherichia coli, Bacillus subtilis, Streptomyces* or *Proteus mirabilis*. The eukaryotic host cell can be fungus such as *Pichia pastoris, Saccharomyces cerevisiae, Schizosaccharomyces, Trichoderma*, etc.; cell of insects such as grass armyworm; cell of plants such as tobacco, etc.; and mammal cell such as BHK cell, CHO cell, COS cell, myeloma cell, etc.

In some embodiment, the host cell of the invention is preferably mammal cell, more preferably BHK cell, CHO cell, NSO cell or COS cell.

The immune neutralizing activity of said humanized anti-BLyS antibody of the invention is assayed by cytological experiments in vitro. The result shows that the humanized anti-BLyS antibody of the invention can inhibit the proliferation of B cell in different degree. Therefore, the invention provides a method for preventing and/or treating diseases caused by over proliferation of B cell, which comprises applying an effective dosage of anti-BLyS antibody of any of claims 1 to 7. The invention further provides the use of said anti-BLyS antibody or humanized anti-BLyS antibody in the preparation of medicaments for preventing and/or treating diseases caused by over proliferation of B cell. The diseases caused by over proliferation of B cell include, but not limited to, SLE, rheumatoid arthritis, ankylosing arthritis or B cell lymphoma cancer.

The invention further provides a pharmaceutical composition, which comprises an effective dosage of any one of the anti-BLyS antibodies or humanized anti-BLyS antibodies of the invention and a pharmaceutically acceptable carrier. The pharmaceutical composition can be prepared by mixing any one of the anti-BLyS antibodies or humanized anti-BLyS antibodies of the invention and one or more pharmaceutically acceptable carrier by conventional method, and can be prepared as pharmaceutical preparation. The "pharmaceutically acceptable carrier" means one or more organic or inorganic, natural or synthetic carriers that are well known to the skilled one in the art, which can promote the stability and clinical application of an antibody by combining with the antibody. Appropriate carriers comprise pharmaceutical acceptable sterile saline solution and aqueous or anhydrous iso-osmotic sterile solution and sterile suspension known to the skilled one in the art. The effective dosage and administration method of the invention depend on many factors, including age, weight, sex, natural health condition, and nutritional status of the patient, intensity of activity of the compound, administration time, metabolic rate, severity of disease and the subjective judgment of the physicians. According to the factors above, the effective dosage and administration method can be easily decided by those skilled in the art.

The pharmaceutical composition of the invention can be prepared using appropriate carriers, excipients and other reagents, which can improve transferring, delivering, tolerance, etc. The formulation used can comprise, for example, tablet, powder, paste, ointment, gel, wax, oil, lipid, vesicle containing lipid, DNA conjugate, etc. The pharmaceutical composition according to the invention can be administrated by any appropriate route, for example by oral, nosal, intradermal, subcutaneous, intramuscular or intravenous.

SPECIFIC EMBODIMENTS

Figure 1:
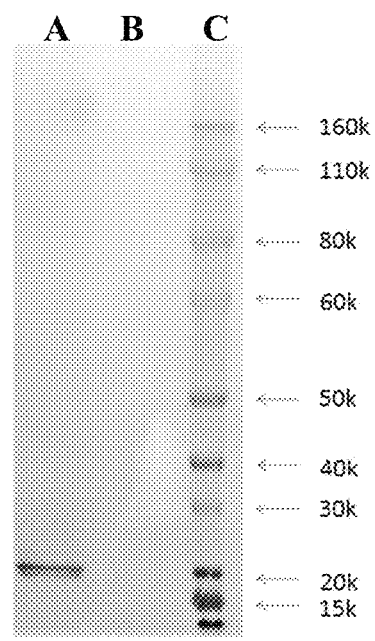
FIG. 1 shows detecting image of SDS-PAGE of example 1, wherein lane A is the protein expressed by the recombinant plasmid of the invention, lane B is recombinant plasmid with blank vector, lane C is protein molecular weight marker.

The embodiments of the invention disclose anti-BLyS antibody and the use thereof. The skilled one in the art can achieve them by making reference to this content and improving the process parameter properly. Specially, all the similar replacement and modification are obvious to the skilled one, and are within the scope of the invention. The product of the invention is described by preferred examples, and those skilled in the art can modify or change and combine properly according to the method described herein without departing from the concept, spirit and scope of the invention, to achieve and apply the technology of the invention.

For further understanding the invention, detailed descriptions to the invention are provided below in combination with examples.

Example 1: Cloning and Expression of Human BLyS Gene

Healthy human peripheral blood was isolated, and the total RNA was extracted and purified with commercial RNA kit (Qiagen Company). The first chain of cDNA was synthesized by reverse transcription with purified total RNA being used as template. The cDNA reaction system was as below:

| | |
|---|---|
| RNase free dH$_2$O | 9.5 μL |
| 5xRT buffer (with 25 mM Mg$^{2+}$) | 4 μL |
| dNTP (10 mM each) | 2 μL |
| RNase Inhibitor (10 U/μL) | 0.5 μL |
| Oligo (dT)$_{20}$ (10 μmol/L) | 1 μL |
| Total RNA template | 2 μL |
| ReverTra Ace | 1 μL |

Sterilized distilled water was added to the system to a total volume of 20 μL.

Reaction conditions were: 30° C. 10 min, 42° C. 30 min, 99° C. 5 min, 4° C. 5 min. The system was placed in an ice bath for 5 min after the reaction was completed.

On the basis of full-length DNA sequence of human BLyS, the cloned secreted BLyS primers P1 and P2 were designed and synthesized. PCR amplification was performed using upstream primer P1 and downstream primer P2 with the cDNA synthesized by reverse transcription being used as template. The nucleotide sequences of P1 and P2 were as below:

P1:
(SEQ ID NO: 59)
5'tacgaagctt gcatcatcat catcatcatg gcggcggctc cggcggcggc tccccgttca gggtccagaa gaa;

P2:
(SEQ ID NO: 60)
5'cgacgtcgac tcacagcagt ttcaatgcac caaaaaatgt gacatc.

The reaction system of PCR amplification was:

| | |
|---|---|
| 10xtaq buffer (with 1.5 mM Mg$^{2+}$) | 5 μL |
| dNTP (5 mM) | 4 μL |
| Upstream primer (100 ng/μL) | 1 μL |
| Downtream primer (100 ng/μL) | 1 μL |
| Template (5-50 ng/μL) | 1 μL |
| Taq enzyme (2 U/μL) | 0.5 μL |

Sterilized distilled water was added to the system to a total volume of 50 μL.

PCR reaction procedure was as follows:

| | | |
|---|---|---|
| predenaturating at 94° C. | 300 s | |
| denaturating at 94° C. | 45 s | |
| annealing at 55° C. | 45 s | } 32 cycles |
| extending at 72° C. | 45 s | |
| extending at 72° C. | 200 s | |

The product of PCR amplification was recovered by gel electrophoresis, double enzyme digested with Sal I and Hind III, and cloned to pCDNA3.1 eukaryotic expression plasmid system. Using the plasmid transformed with blank vector as control, 3 days after transfecting 293T cells (China Center for Type Culture Collection), the supernatant of culture medium was collected, and purified by His affinity chromatography to obtain purified his-hBLyS protein. It was assayed by SDS-PAGE. The result was shown in FIG. 1.

It can be seen from the result in FIG. 1 that, proteins were expressed by the recombinant plasmid of the invention, while no clear protein expression band were found for recombinant plasmid of blank vector. The recombinant plasmid protein of the invention was of about 23 Kb, close to the molecular weight of 23 Kb deduced according to human BLyS amino acid sequence.

Example 2: Assaying the Binding Capacity to Receptor on BJAB Cell

1. Labeling His-hBLyS recombinant protein with biotin.

Purified His-hBLyS recombinant protein obtained from example 1 was mixed with biotin-xx-NHS dissolved in DMSO, in a weight-to-volume ratio of 1:4 in ng/mL, and placed at room temperature for 1 hour. The reaction mixture was chromatographed through a gel column to isolate the biotin-labeled his-hBLyS and free biotin.

2. Binding biotin-labeled his-hBLyS recombinant protein to BJAB cell.

The isolated biotin-labeled his-hBLyS recombinant proteins were divided into four groups having different concentrations of 25 ng/mL, 50 ng/mL, 100 ng/mL and 200 ng/mL, mixed with 1×10$^6$ human Burkitt lymphoma cells (BJAB) respectively, incubated at 4° C. for 15 min, washed with PBS for 3 times, added with streptavidin-allophycocyanin (SA-APC) to reach a final concentration of 0.2 μg/mL, and incubated at 4° C. for 20 min. After washing with PBS for 3 times, it was assayed by flow cytometer. The result was shown in FIG. 2.

Figure 2:
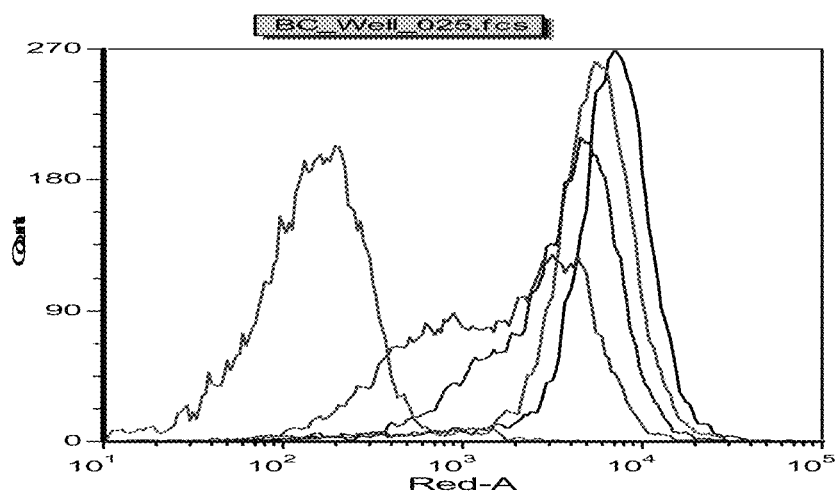
FIG. 2 shows flow cytometry graph of combination of his-hBLyS recombinant protein labeled by biotin in different concentrations and BJAB cells of example 2, wherein the tallest peak represents the group of his-hBLyS recombinant protein labeled by biotin at 200 ng/mL, the second tallest peak represents the group of his-hBLyS recombinant protein labeled by biotin at 100 ng/mL, one of the third tallest peak on the righr represents the group of his-hBLyS recombinant protein labeled by biotin at 50 ng/mL, the lowest peak represents the group of his-hBLyS recombinant protein labeled by biotin at 25 ng/mL, the other one of the third tallest peak on the left represents the group without biotin labeled his-hBLyS recombinant protein and only containing SA-APC.

It can be seen from the result of FIG. 2 that, the biotin-labeled recombinant human BLyS protein can bind to BJAB cell at different concentrations.

Example 3: Immunizing Mouse

The his-hBLyS recombinant protein obtained from example 1 was used as antigen to mix with the same amount of immunologic adjuvant (Freund adjuvant). 4 female FVB mice of 6 weeks old were tested, 3 of which were immunized, and the other one was used for control mimic experiment. After first immunization, a reinforce immunization was given once a week. Before the last reinforce immunization, blood was drawn from the tail vein of the immunized mice. The serum was mixed with biotin-labeled his-hBLyS recombinant protein (with a concentration of 50 ng/mL) and incubated at room temperature for 20 min. Then, the mixture was incubated with BJAB cell at 4° C. for 15 min, washed with normal saline for 3 times, added with streptavidin-allophycocyanin of 0.2 μg/mL and incubated at 4° C. for 15 min. After washing with normal saline for 3 times, the sample was assayed by flow cytometer to test whether the serum of immunized mouse can inhibit BLyS from binding to its receptor BR3-Fc. The result was shown in FIG. 3.

Figure 3:
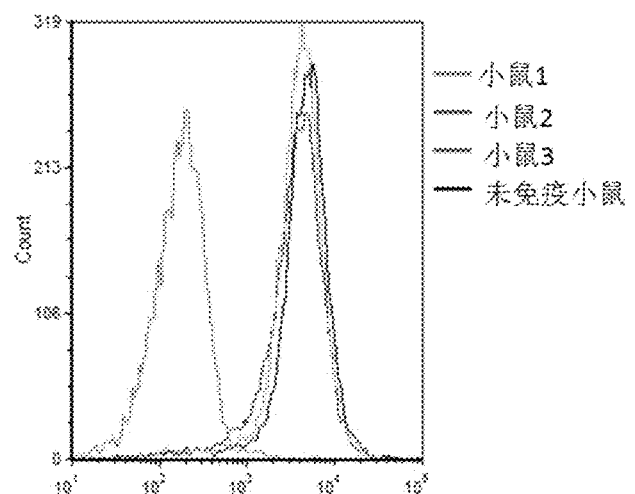
FIG. 3 shows flow cytometry graph of combination of serum of immunized mice and BJAB cells of example 3.

It can be seen from the result of FIG. 3 that, the serum obtained from mouse 1 of three immunized mice can effectively inhibit the binding of biotin-labeled his-hBLyS recombinant protein to BJAB cell. Therefore, mouse 1 was selected as follow-up experimental individual to conduct the further fusion experiments.

Example 4: Cell Fusion and Screening of Monoclonal Hybridoma Cell

After the last reinforce immunization, the lymph node at thigh root of the mouse was harvested, and ground in normal saline. The suspension riched in B cell was taken and fused with myeloma cell SP2/0 by electroporating with routine method. The fused cells were distributed in 96-well plate, and incubated in complete medium RPMI-1640 containing HAT under the condition of 5% CO$_2$ at 37° C. By enzyme labelled method, 211 clones that secreted the antibodies capable of binding to BLyS protein were screened out of different monoclonal hybridoma cells.

Figure 4:
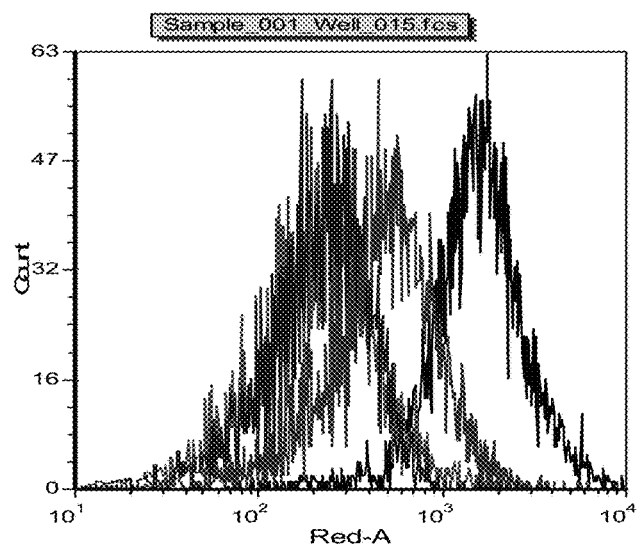
FIG. 4 shows flow cytometry graph of combination of antibody secreted by monoclonal hybridoma cell and BLyS receptor on BJAB cell of example 4, wherein the first peak on the right represents the group of IgG negative control, the first peak on the left represents the group without biotin labeled his-hBLyS recombinant protein and only containing SA-APC, the second peak on the right represents the group of monoclonal hybridoma cell 3H9, the second peak on the left represents the group of monoclonal hybridoma cell 13G8.
Figure 5:
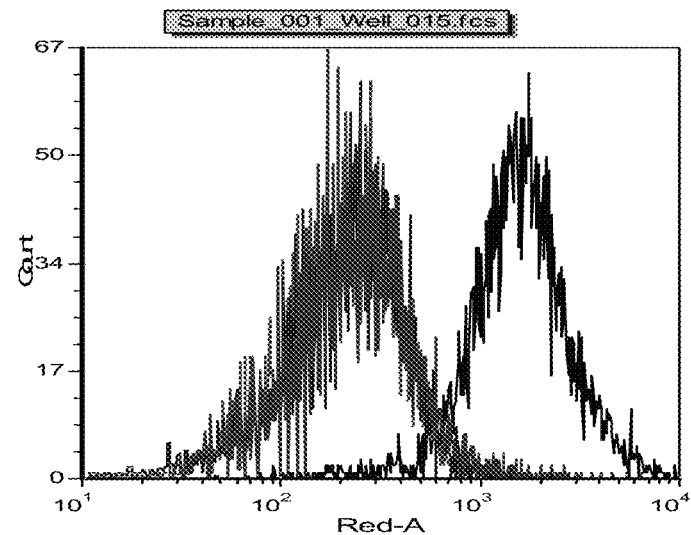
FIG. 5 shows flow cytometry graph of combination of antibody secreted by monoclonal hybridoma cell and BLyS receptor on BJAB cell of example 4, wherein the right-most peak represents the group of IgG negative control, the three largely overlapping peaks on the left represent the group of monoclonal hybridoma cell 1D12, monoclonal hybridoma cell 2B10, and monoclonal hybridoma cell 2G3.
Figure 6:
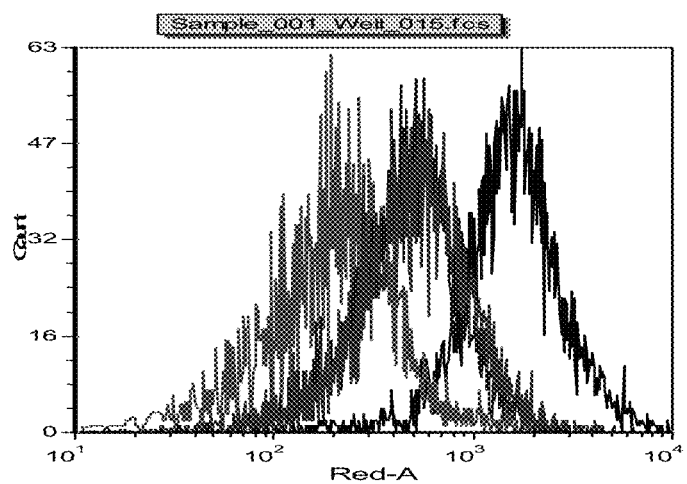
FIG. 6 shows flow cytometry graph of combination of antibody secreted by monoclonal hybridoma cell and BLyS receptor on BJAB cell of example 4, wherein the first peak on the right represents the group of IgG negative control, the first peak on the left represents the group of monoclonal hybridoma cell 5A5, the second peak on the right represents the group of monoclonal hybridoma cell 1D7, the second peak on the left represents the group of monoclonal hybridoma cell 4D3.

The antibodies produced by 211 clones which can bind to BLyS protein were mixed with biotin-labeled his-hBLyS recombinant protein respectively and incubated at room temperature for 20 min. Then, the mixture was incubated with BJAB cells at 4° C. for 15 min, washed with normal saline for 3 times, added with streptavidin-allophycocyanin of 0.2 μg/mL and incubated at 4° C. for 15 min. After washing with normal saline for 3 times, the sample was assayed on a flow cytometer to screen out the monoclonal hybridoma cells which can inhibit the binding of biotin-labeled his-hBLyS recombinant protein to BJAB cells. As a result, the antibodies secreted by 11 monoclonal hybridoma cells can inhibit the binding of biotin-labeled his-hBLyS recombinant protein to BLyS receptor on BJAB in different degrees, as shown in table 1. The inhibition capacity of antibodies secreted by monoclonal hybridoma cells named as 1D12, 2B10, 2G3, 5A5 and 13G8 was stronger than that of antibodies secreted by monoclonal hybridoma cells named as 3H9, 1D7, and 4D3. The assay results of 1D12, 2B10, 2G3, 5A5 and 13G8 were shown in FIGS. 4 to 6.

TABLE 1

Subtypes of antibodies secreted by cells which inhibit binding of biotin-labeled his-hBLyS recombinant protein to BLyS receptor on BJAB.

| | Clone | Subtype |
|---|---|---|
| 1 | 1D12 | IgG2b/kappa |
| 2 | 2B10 | IgG2b/kappa |
| 3 | 2G3 | IgG2a/kappa |
| 4 | 5A5 | IgG3/kappa |
| 5 | 13G8 | IgG2a/kappa |
| 6 | 1D7 | IgG2a/kappa |
| 7 | 2A9 | IgG1/kappa |
| 8 | 4D3 | IgG2a/kappa |
| 9 | 5E5 | IgG3/kappa |
| 10 | 5F4 | IgG1/kappa |
| 11 | 5H5 | IgG2b/kappa |

Example 5: Testing the Binding to Other Protein of Tumor Necrosis Factor (TNF) Family For further testing the binding specificity of candidate antibodies, 1 μg/mL his-hBLyS recombinant protein, tumor necrosis factor-α (TNF-α), tumor necrosis factor-β (TNF-β), and BSA were introduced to 96 wells ELISA plate, and stood overnight at 4° C. in carbonate coating buffer of 0.05 M with Ph 9.0. The next day, the solution in the wells was abandoned, and the wells were washed with washing buffer for 3 times. Then, PBS solution containing 3% BSA was added and sealed for 20 min. After washing with washing buffer for 3 times, 100 μL diluted antibodies secreted by monoclonal hybridoma cells 1D12, 2B10, 2G3, 5A5 and 13G8 were added, incubated for 1 hour at room temperature and washed with washing buffer for 3 times. Goat anti-mouse antibody was crosslinked with Horseradish Peroxidase (HRP) diluted with washing buffer at 1:10000 times, and incubated for 1 hour at room temperature. After washing with washing buffer for 3 times, 50 μL 3,3',5,5'-Tetramethylbenzidine (TMB) substrate solution was added for color development, and reacted at room temperature for 10 min. Then the reaction was terminated with 25 μL sulfuric acid solution of 0.5 M. Absorbance at 450 nm was read. The statistical result was shown in FIG. 7.

Figure 7:
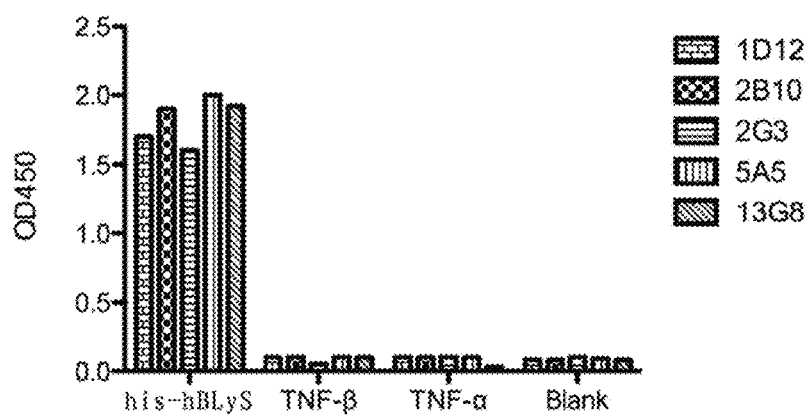
FIG. 7 shows enzyme linked immunosorbent assay result of antibodies secreted by monoclonal hybridoma cell 1D12, 2B10, 2G3, 5A5 and 13G8 of example 4, and his-hBLyS recombinant proteain and protein of tumor necrosis factor (TNF) family.

It can be seen from FIG. 7 that, antibodies secreted by monoclonal hybridoma cells 1D12, 2B10, 2G3, 5A5 and 13G8 all recognize and bind to BLyS, but none of them recognizes TNF-α or TNF-β.

Example 6: Determination of the Sequence of the Variable Region of Antibody Secreted by Monoclonal Hybridoma Cell The monoclonal hybridoma cells 1D12, 2B10, 2G3, 5A5 and 13G8 obtained by screening were incubated. Cells were collected by centrifuging at 1000 rpm. The first chain of cDNA was synthesized by the inverse transcription of individual hybridoma cell RNA extracted according to the method of example 1. The DNA sequence of variable region corresponding to hybridoma cells was amplified with the synthesized first chain of cDNA being used as a template. The primer sequences used in the amplification reaction were as below:

The primers required for amplification of heavy chain was as follows:

```
primer 1:
                                  (SEQ ID NO: 61)
5'atg g(a/g)a tg(c/g) agctg(t/g) gt(ca) at(c/g) ctc tt;

primer 2:
                                  (SEQ ID NO: 62)
5'ggg gatatc cacc atg (a/g)ac ttc ggg (t/c) tg agc t(tg)g gtt tt;
and primer 3:
                                  (SEQ ID NO: 63)
5'ggg tatatc cacc atg gct gtc ttg gggctg ctatct.
```

The primers required for amplification of light chain was as follows:

```
primer 1:
(SEQ ID NO: 64)
5' atg gag aca gac aca ctcctgctat;

primer 2:
(SEQ ID NO: 65)
5'atg gattttcaa gtg cag a tt ttc ag;

primer 3:
(SEQ ID NO: 66)
5'atg gag (t/a)ca ca(g/t)(t/a)ct cag gtc ttt (g/a)t a;
and primer 4:
(SEQ ID NO: 67)
5'atg (g/t)cc c(a/t) (g/a) ct cag (c/t)t(c/t)

ct(t/g)gt.
```

The amplification reaction system was:

| | |
|---|---|
| 10xPCR buffer (with 25 mM $Mg^{2+}$) | 5 μL |
| dNTP (5 mM) | 1 μL |
| Primer mixture of heavy chain or primer mixture of light chain (each primer of 100 ng/μL) | 1 μL |
| cDNA (5-50 ng/μL) | 1 μL |
| Taq enzyme (2 U/μL) | 1 μL |

Sterilized distilled water was added to the system to reach a total volume of 50 μL.

PCR reaction procedure was:

| | | |
|---|---|---|
| predenaturating at 95° C. | 10 min | |
| denaturating at 94° C. | 1 min | |
| annealing at 55° C. | 1 min | } 30 cycles |
| extending at 72° C. | 115 min | |
| extending at 72° C. | 10 min | |

The PCR amplification product was recovered by gel electrophoresis, and sent to biological company for sequencing. Serial analysis was conducted for the obtained sequences according to www.expasy.ch. The amino acid sequences of light chain variable region and heavy chain variable region were shown in table 2. Kabat classification analysis was conducted based on the derived amino acid sequences to determine the FR region and CDR region of light chain and heavy chain of individual hybridoma cells 1D12, 2B10, 2G3, 5A5 and 13G8. The amino acid sequences of the light chain variable region and the amino acid sequences of the heavy chain variable region of individual hybridoma cells 1D12, 2B10, 2G3, 5A5 and 13G8 were shown in table 2:

TABLE 2

Amino acid sequences of light chain variable region and heavy chain variable region of anti-BLyS antibody.

|      | Amino acid sequences of light chain variable region | Amino acid sequences of heavy chain variable region |
|------|-----------------------------------------------------|-----------------------------------------------------|
| 1D12 | SEQ ID NO. 31                                       | SEQ ID NO. 32                                       |
| 2B10 | SEQ ID NO. 33                                       | SEQ ID NO. 34                                       |
| 2G3  | SEQ ID NO. 35                                       | SEQ ID NO. 36                                       |
| 5A5  | SEQ ID NO. 37                                       | SEQ ID NO. 38                                       |
| 13G8 | SEQ ID NO. 39                                       | SEQ ID NO. 40                                       |

Example 7: The Humanization of Anti-BLyS Antibody

Humanized transformation was performed to the variable region sequences of antibodies secreted by individual hybridoma cells.

The procedure of the humanized transformation mainly involved in the following key steps.

A. The gene sequences of antibodies secreted by individual hybridoma cells were compared with the antibody gene sequences of human embryonic system to find the sequences having high homology.

B. The affinity with HLA-DR was tested by analysis in silicon to select the frame sequence of human embryonic system having low affinity.

C. The frame amino acid sequences of variable region and periphery thereof were analyzed by applying molecular docking utilizing computer simulation technology to investigate the form of stereoscopic combination. By calculating electrostatic force, van der waals force, hydrophobic and hydrophilic properties, and entropy value, the key amino acid individuals in gene sequence of antibody secreted by individual hybridoma cells which may interact with BLyS and maintain the spacial framework were analyzed, and were grafted back to the selected gene frame of human embryonic system. On this basis, 4 different humanized anti-BLyS antibodies were obtained. The sequences of light chain variable region and heavy chain variable region of them were shown in table 3.

TABLE 3

Sequences of light chain variable region and heavy chain variable region of humanized anti-BLyS antibody.

|     | Amino acid sequences of light chain variable region | Amino acid sequences of heavy chain variable region |
|-----|-----------------------------------------------------|-----------------------------------------------------|
| I   | SEQ ID NO. 41                                       | SEQ ID NO. 42                                       |
| II  | SEQ ID NO. 43                                       | SEQ ID NO. 44                                       |
| III | SEQ ID NO. 45                                       | SEQ ID NO. 46                                       |
| IV  | SEQ ID NO. 47                                       | SEQ ID NO. 48                                       |

Example 8: The Construction of Expression Vector of Humanized Anti-BLyS Antibody The heavy chain constant region Fc fragment was amplified from human blood cell by using upstream primer VH5 and downstream primer VH3. The light chain k constant region was amplified from human blood cell by using upstream primer VL5 and downstream primer VL3. Xho I and Age I endouncleae sites were introduced in heavy chain. Sma I and Dra III endouncleae sites were introduced in light chain fragment. pCDNA 3.1 plasmid was incorporated, and correct clone was confirmed by sequencing. Sequential experimental materials were all obtained by extracting from the cells which were tranfected by this series of plasmid. The nucleotide sequences of VH5, VH3, VL5 and VL3 were as below:

VH5:
(SEQ ID NO: 68)
5'gcggaattc(c/g)a ggtg(a/c)agct(g/t)c a(c/g)(c/g)a (a/g)tc(a/t)gg;

VH3:
(SEQ ID NO: 69)
5'accgccggat ccaccaccgc ccg agccacc gccacctgcg gagacgatga cc(a/g)tggtccc;

VL5:
(SEQ ID NO: 70)
5'ggtggtggatccggeggtgg cggttccgacattgtgatgacccagtc tcca;

VL3:
(SEQ ID NO: 71)
5'ggatacagttggtgcagcctcgagctacc gttt.

Four humanized antibodies were obtained, which were named as BLyS-I, BLyS-II, BLyS-III and BLyS-IV respectively.

Example 9: Humanized Anti-BLyS Antibodies Inhibit the Prolification of B Cell In Vitro B cells were extracted by CD19 labeled MACS magnetic beads from human peripheral blood, and were subcultured into 96-well plate in 100,000 per plate and incubated. Recombinant BLyS (10 ng/mL) and Fab fragment of goat anti-human IgM (4 μg/mL) were introduced into complete medium to stimulate the growth of B cell. Different humanized anti-BLyS antibodies having different concentrations obtained from example 8 were introduced into the medium and incubated for 6 days. Thereafter, B cell was counted by Celltiter Glo from Promega Company. The value (RLU) was counted by fluorescence. The result was shown in FIG. 13.

Figure 8:
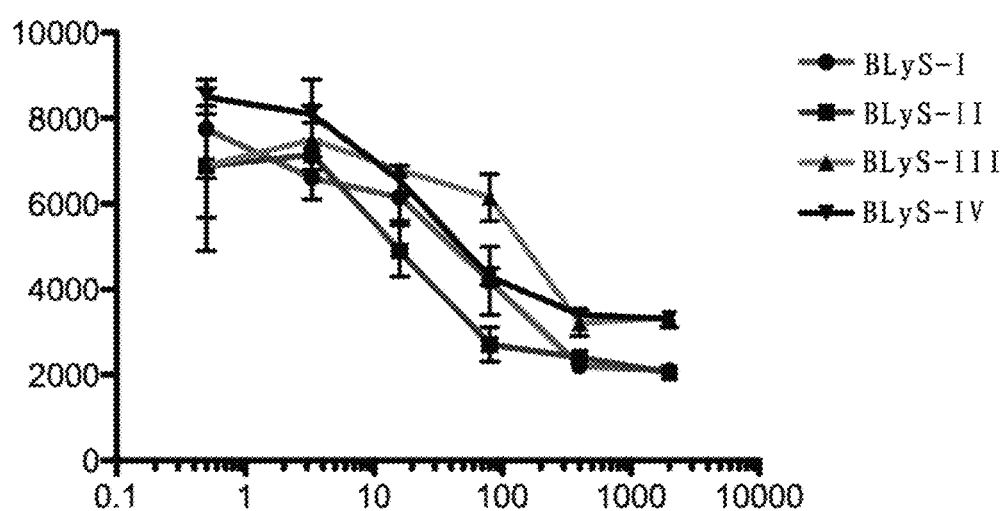
FIG. 8 shows the result of in vitro inhibiting prolificaiton of B cell by the humanized anti-BLyS antibody of example 9, wherein the horizontal axis represents concentration of humanized anti-BLyS antibody, the vertical axis represents fluorescence value.

It can be seen from FIG. 8 that, four humanized anti-BLyS antibodies BLyS-I, BLyS-II, BLyS-III and BLyS-IV prepared in example 8 can inhibit the growth of B cell in different degrees.

The above examples are only used for helping understand the method of the invention and the concept thereof. For the normal skilled one in the art, many revisions and modifications can be made to the invention, which still fall into the scope of the invention, without departing from the principle of the invention.

Example 10: Pharmacodynamics Study of Humanized Anti-BLyS Antibody In Vivo

1) Determining the dosage of BLyS for stimulating proliferation of B cell.

Recombinant BLyS having different concentrations were injected into caudal vein of mice. The body weight (gram), spleen weight (mg), and lymph node weight (mg) of the mouse were measured after a week. The results were shown in table 4.

TABLE 4

| Group | ID | Body weight, gram | Spleen weight, mg | lymph node weight, mg | Average |
|---|---|---|---|---|---|
| PBS | 1 | 17.8 | 64.5 | 7.9 | 7.6 |
|  | 2 | 17.9 | 128 | 7.3 |  |
| 0.1 mg/kg | 3 | 18.4 | 99.4 | 7.8 | 7.8 |
|  | 4 | 17.9 | 98.6 | 7.8 |  |
| 0.3 mg/kg | 5 | 17.9 | 107 | 7.4 | 8.75 |
|  | 6 | 17.5 | 98.6 | 10.1 |  |
| 0.9 mg/kg | 7 | 18.1 | 115 | 12.4 | 10.2 |
|  | 8 | 16.6 | 79.6 | 8 |  |
| 2.7 mg/kg | 9 | 18 | 81.6 | 10.6 | 12.3 |
|  | 10 | 18.2 | 89.3 | 14 |  |

The results showed that self-produced BLyS of 0.3 mg/Kg can effectively stimulate the growth of B cell in vivo. The weight of lymph node can be used as the main pharmacodynamic evaluation indicator for evaluating the proliferation of B cell stimulating by BLyS. This was mainly due to the fact that 50% of the lymph node were B cell, and the ratio of B cell became higher after being stimulated by BLyS.

2) In vivo study of inhibiting effect of anti-BLyS antibody on BlyS

Figure 9:
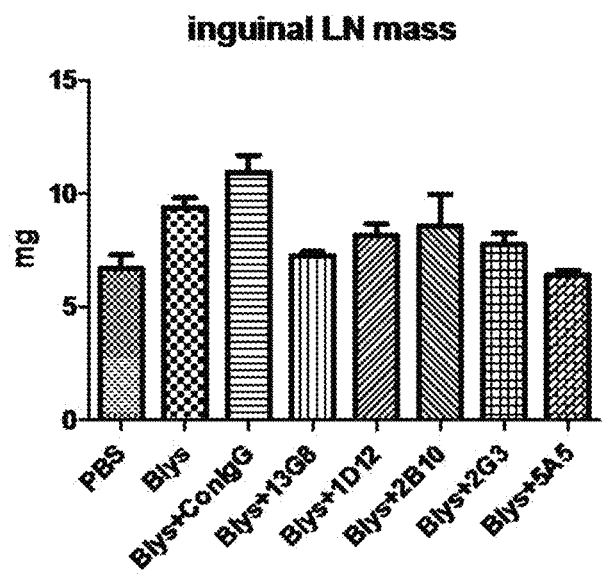
FIG. 9 shows the inhibition effect of candidate antibody molecule on lymph node hyperplasia induced by BLyS.
Figure 10:
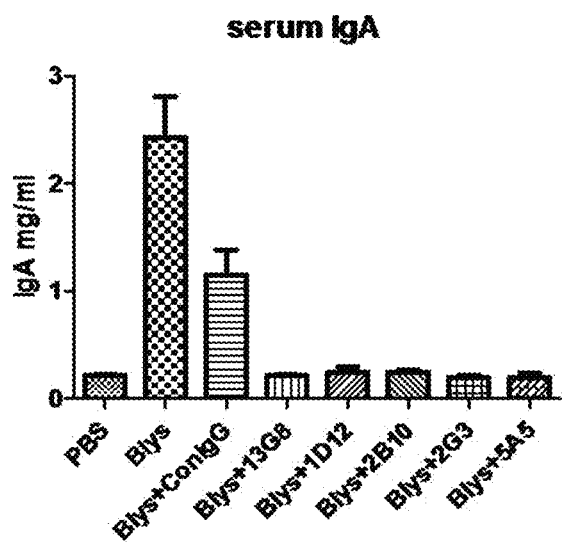
FIG. 10 shows the inhibition effect of candidate antibody molecule on increase of serum IgA induced by BLyS.

On this basis, the BLyS of 0.3 mg/kg was mixed with mouse 1D12, 2B10, 2G3, and 5A5 and human BLyS-I (13G8) of 0.05 mg/kg. Then, their lymph node weight and IgA content in serum were measured (see FIG. 9 and FIG. 10).

The result showed: mouse 1D12, 2B10, 2G3, and 5A5 and human BlyS-I (13G8) can effectively inhibit the effect of BLyS.

What is claimed is:

1. An anti-B lymphocyte Stimulator (anti-BlyS) antibody, wherein the amino acid sequences of the light chains CDR1, CDR2 and CDR3, and the amino acid sequences of the heavy chains CDR1, CDR2 and CDR3 are selected from one of the following groups:
   (a) SEQ ID NOs: 1, 2, 3, 4, 5, and 6, respectively;
   (b) SEQ ID NOs: 7, 8, 9, 10, 11, and 12, respectively;
   (c) SEQ ID NOs: 13, 14, 15, 16, 17, and 18, respectively;
   (d) SEQ ID NOs: 19, 20, 21, 22, 23, and 24, respectively; and
   (e) SEQ ID NOs: 25, 26, 27, 28, 29, and 30, respectively.

2. The anti-BLyS antibody according to claim 1, wherein the amino acid sequences of the light chain variable region and the amino acid sequences of the heavy chain variable region of the anti-BLyS antibody are selected from the group consisting of:
   a: amino acid sequences as shown by SEQ ID NO: 31 and SEQ ID NO: 32;
   b: amino acid sequences as shown by SEQ ID NO: 33 and SEQ ID NO: 34;
   c: amino acid sequences as shown by SEQ ID NO: 35 and SEQ ID NO: 36;
   d: amino acid sequences as shown by SEQ ID NO: 37 and SEQ ID NO: 38; and
   e: amino acid sequences as shown by SEQ ID NO: 39 and SEQ ID NO: 40.

3. The anti-BLyS antibody according to claim 1, wherein said antibody is humanized.

4. The anti-BLyS antibody according to claim 3, wherein said antibody further comprises a human light chain constant region and a human heavy chain constant region, and the light chain variable region and the heavy chain variable region connect to the human light chain constant region and the human heavy chain constant region respectively.

5. The anti-BLyS antibody according to claim 4, wherein the human light chain constant region is a human light chain κ constant region.

6. The anti-BLyS antibody according to claim 4, wherein the human heavy chain constant region is a human heavy chain Fc fragment.

7. The anti-BLyS antibody according to claim 1, wherein the amino acid sequences of the light chain variable region and the amino acid sequences of the heavy chain variable region of the anti-BLyS antibody are selected from the group consisting of:
   I: amino acid sequences as shown by SEQ ID NO: 41 and SEQ ID NO: 42;
   II: amino acid sequences as shown by SEQ ID NO: 43 and SEQ ID NO: 44;
   III: amino acid sequences as shown by SEQ ID NO: 45 and SEQ ID NO: 46; and
   IV: amino acid sequences as shown by SEQ ID NO: 47 and SEQ ID NO: 48.

8. A DNA molecule encoding the anti-BLyS antibody of claim 1.

9. The DNA molecule according to claim 8, wherein the DNA molecule has a nucleotide sequence selected from one of SEQ ID NOs: 49-58.

10. A recombinant DNA vector, comprising the DNA molecule of claim 8.

11. A host cell, comprising the recombinant DNA vector of claim 10.

12. A method for preparing an anti-BLyS antibody, comprising:
    incubating the host cell of claim 11, and obtaining the antibody.

13. A method for treating diseases caused by over proliferation of B cells in an individual in need thereof, comprising administrating to said individual an effective dosage of the anti-BLyS antibody of claim 1.

14. The method according to claim 13, wherein the diseases caused by over proliferation of B cells are selected from systemic lupus erythematosus, rheumatoid arthritis, ankylosing arthritis or B cell lymphoma.

15. A pharmaceutical composition, comprising an effective dosage of the antibody of claim 1 and a pharmaceutically acceptable carrier.

* * * * *